United States Patent
Baltimore et al.

(10) Patent No.: US 9,006,195 B2
(45) Date of Patent: Apr. 14, 2015

(54) REGULATION OF HEMATOPOIETIC STEM CELL FUNCTIONS THROUGH MICRORNAS

(75) Inventors: David Baltimore, Pasadena, CA (US); Ryan M. O'Connell, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/230,673

(22) Filed: Sep. 12, 2011

(65) Prior Publication Data

US 2012/0065245 A1    Mar. 15, 2012

Related U.S. Application Data

(60) Provisional application No. 61/382,429, filed on Sep. 13, 2010.

(51) Int. Cl.
A61K 31/70    (2006.01)
A61K 31/7105    (2006.01)

(52) U.S. Cl.
CPC ....... *A61K 31/7105* (2013.01); *C12N 2310/141* (2013.01)

(58) Field of Classification Search
CPC combination set(s) only.
See application file for complete search history.

(56) References Cited

U.S. PATENT DOCUMENTS

2008/0171715 A1\* 7/2008 Brown et al. .................. 514/44
2011/0280861 A1\* 11/2011 Scadden et al. ............ 424/130.1

OTHER PUBLICATIONS

O'Connell, et al. (2010) PNAS, v.107(32):14235-40.\*
Klusmann, et al. (2010) Genes and Dev., v.24:478-90.\*
Ambros, The functions of animal microRNAs. Nature 431: 350-355 (2004).
Balazs et al., Endothelial protein C receptor (CD201) explicitly identifies hematopoietic stem cells in murine bone marrow. Blood 107: 2317-2321 (2006).
Bartel & Chen, Micromanagers of gene expression: The potentially widespread influence of metazoan microRNAs. Nat. Rev. Genet. 5: 396-400 (2004).
Bartel, MicorRNAs. Cell 116: 281-297 (2004).
Bousquet et al. Myeloid cell differentiation arrest by miR-125b-1 in myelodysplastic syndrome and acute myeloid leukemia with the t(2;11)(p21;q23) translocation. J Exp Med., 205: 2499-2506 (2008).
Calin GA, et al. Frequent deletions and down-regulation of micro-RNA genes miR15 and miR16 at 13q14 in chronic lymphocytic leukemia. Proc. Natl. Acad. Sci. USA. 99: 15524-15529 (2002).
Calin, et al., Human microRNA genes are frequently located at fragile sites and genomic regions involved in cancers. Proc. Natl. Acad. Sci. USA 101, 2999-3004 (2004).
Cammarata et al., Differential expression of specific microRNA and their targets in acute myeloid leukemia. Am J Hematol., 85: 331-339 (2010).
Chen, MicroRNAs modulate hematopoietic lineage differentiation, Science 303, 83-86 (2004).
Chendrimada et al., TRBP recruits the Dicer complex to Ago2 for microRNA processing and gene silencing, Nature 436, 740-4 (2005).
Cobb et al., T cell lineage choice and differentiation in the absence of the RNase III enzyme Dicer. J. Exp. Med., 201: 1367-1373 (2005).
Costinean et al., Pre-B cell proliferation and lymphoblastic leukemia/high-grade lymphoma in E(mu)-miR155 transgenic mice. Proc. Natl. Acad. Sci. USA., 103: 7024-7029 (2006).
Couzin, Breakthrough of the year. Small RNAs make big splash. Science 298(5602):2296-2297 (2002).
Deneault et al., A functional screen to identify novel effectors of hematopoietic stem cell activity. Cell 137: 369-379 (2009).
Dennis, Small RNAs: the genome's guiding hand? Nature, 420(6917): 732 (2002).
Esau et al., MicroRNA-143 regulates adipocyte differentiation, J. Biol. Chem. 279: 52361-52365 (2004).
Farh et al., The widespread impact of mammalian MicroRNAs on mRNA repression and evolution. Science 310: 1817-21 (2005).
Fazi et al., A minicircuitry comprised of microRNA-223 and transcription factors NFI-A and C/EBPalpha regulates human granulopoiesis. Cell 123: 819-831 (2005).
Fontana et al., MicroRNAs 17-5p-20a-106a control monocytopoiesis through AML1 targeting and M-CSF receptor upregulation. Nat. Cell. Biol., 9: 775-787 (2007).
Georgantas et al., CD34+ hematopoietic stem-progenitor cell microRNA expression and function: A circuit diagram of differentiation control. Proc. Natl. Acad. Sci. USA. 104: 2750-2755 (2007).
Gregory et al., The Microprocessor complex mediates the genesis of microRNAs. Nature 432: 235-40 (2004).
Gruber et al. Ars2 links the nuclear cap-binding complex to RNA interference and cell proliferation. Cell 138: 328-339 (2009).
Han et al., microRNA-29a induces aberrant self-renewal capacity in hematopoietic progenitors, biased myeloid development, and acute myeloid leukemia. J. Exp. Med., 207: 475-489 (2010).
He et al., A microRNA polycistron as a potential human oncogene. Nature 435, 828-833 (2005).
Johnnidis et al., Regulation of progenitor cell proliferation and granulocyte function by microRNA-223. Nature 451: 1125-1129 (2008).
Kidner & Martienssen, Macro effects of microRNAs in plants. Trends Genet, 19(1): 13-16 (2003).
Kiel et al. SLAM family receptors distinguish hematopoietic stem and progenitor cells and reveal endothelial niches for stem cells. Cell 121: 1109-1121 (2005).
Klein et al. The DLEU2/miR-15a/16-1 cluster controls B cell proliferation and its deletion leads to chronic lymphocytic leukemia. Cancer Cell 17: 28-40 (2010).

(Continued)

*Primary Examiner* — Jennifer McDonald
(74) *Attorney, Agent, or Firm* — Knobbe, Martens, Olson & Bear LLP

(57) ABSTRACT

The present disclosure relates to regulation of functions of hematopoietic stem cells (HSCs) by delivering of miRNAs, including miR-125b, miR-126, and miR-155, to HSCs. For example, in some embodiments, blood output in a mammal can be increased by administering miR-125b, miR-126, and/or miR-155 oligonucleotides. Also disclosed are methods for promoting hematopoietic stem cell engraftment and method for treating a myeloproliferative disorder.

13 Claims, 20 Drawing Sheets

(56) References Cited

OTHER PUBLICATIONS

Klusmann et al., miR-125b-2 is a potential oncomiR on human chromosome 21 in megakaryoblastic leukemia. Genes Dev., 24: 478-490 (2010).

Koralov SB, et al. Dicer ablation affects antibody diversity and cell survival in the B lymphocyte lineage. Cell 132: 860-874 (2008).

Krutzfeldt et al., Silencing of microRNAs in vivo with 'antagomirs'. Nature 438: 685-689 (2005).

Lecellier et al., A Cellular MicroRNA Mediates Antiviral Defense in Human Cells. Science 308: 557-60 (2005).

Lee et al., MicroRNA genes are transcribed by RNA polymerase II. EMBO J. 23: 4051-4060 (2004).

Lu, J. et al., MicroRNA expression profiles classify human cancers. Nature 435: 834-838 (2005).

Matteucci et al., Synthesis of deoxyoligonucleotides on a polymer support J. Am. Chem. Soc. 103: 3185-3191 (1981).

Melton et al., Opposing microRNA families regulate self-renewal in mouse embryonic stem cells. Nature 463: 621-626 (2010).

Monticelli, et al., MicroRNA profiling of the murine hematopoietic system. Genome Biol. 6: R71 (2005).

Muljo et al., Aberrant T cell differentiation in the absence of Dicer. J. Exp. Med. 202: 261-269 (2005).

O'Connell et al., Sustained expression of microRNA-155 in hematopoietic stem cells causes a myeloproliferative disorder. J. Exp. Med. 205: 585-594 (2008).

O'Connell et al., Physiological and pathological roles for microRNAs in the immune system. Nat. Rev. Immunol., 10:111-122 (2010).

O'Connell et al., Inositol phosphatase SHIP1 is a primary target of miR-155. Proc. Natl. Acad. Sci. USA 106: 7113-7118 (2009).

O'Donnell et al., c-Myc-regulated microRNAs modulate E2F1 expression. Nature 435: 839-843 (2005).

Orkin & Zon. Hematopoiesis: An evolving paradigm for stem cell biology. Cell 132: 631-644 (2008).

Park et al., Bmi-1 is required for maintenance of adult self-renewing haematopoietic stem cells. Nature 423: 302-305 (2003).

Pasquinelli et al., MicroRNAs: a developing story. Curr. Opin. Genet. Dev. 15: 200-205 (2005).

Poy et al., A pancreatic islet-specific microRNA regulates insulin secretion. Nature 432, 226-230 (2004).

Ramalho-Santos et al., "Stemness:" Transcriptional profiling of embryonic and adult stem cells. Science 298: 597-600 (2002).

Santaguida et al., JunB protects against myeloid malignancies by limiting hematopoietic stem cell proliferation and differentiation without affecting self-renewal. Cancer Cell 15: 341-352 (2009).

Savona & Talpaz. Getting to the stem of chronic myeloid leukaemia. Nat. Rev. Cancer, 8: 341-350 (2008).

Sullivan & Ganem, MicroRNAs and viral infection. Mol. Cell 20, 3-7 (2005).

Traggiai et al., Development of a human adaptive immune system in cord blood cell-transplanted mice. Science. 304:104-107 (2004).

Wang et al., The endothelial-specific microRNA miR-126 governs vascular integrity and angiogenesis. Dev. Cell, 15: 261-271 (2008).

Winter et al. Many roads to maturity: microRNA biogenesis pathways and their regulation. Nat. Cell. Biol., 11: 228-234 (2009).

Xiao et al., MiR-150 controls B cell differentiation by targeting the transcription factor c-Myb. Cell. 131: 146-159 (2007).

Zeng & Cullen, Sequence requirements for micro RNA processing and function in human cells. RNA, 9(1): 112-123 ((2003).

Zhang et al., PTEN maintains haematopoietic stem cells and acts in lineage choice and leukaemia prevention. Nature 441: 518-522 (2006).

\* cited by examiner

A.

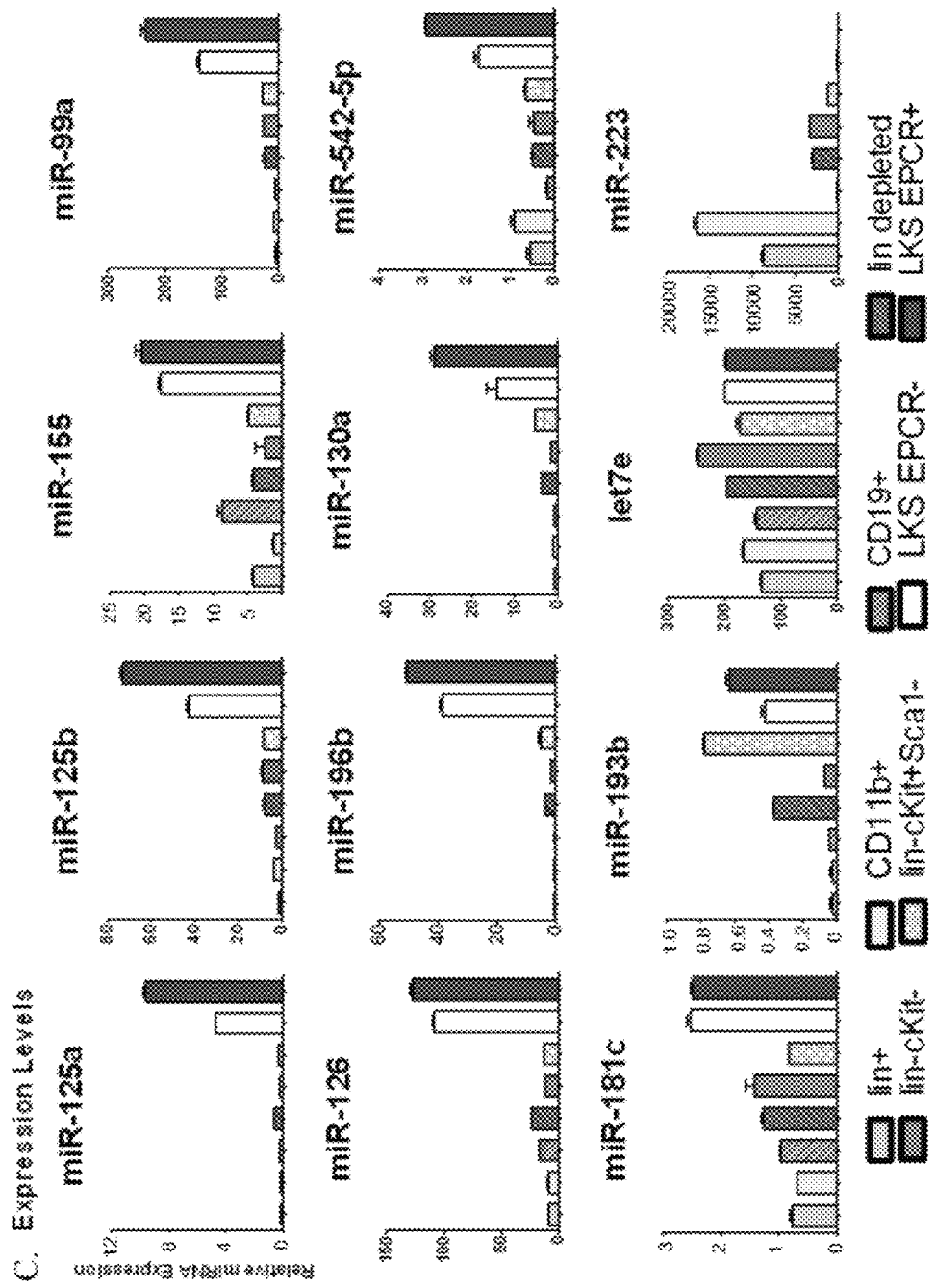

A.

B.

C.

C.

D.

B.

C.

REGULATION OF HEMATOPOIETIC STEM CELL FUNCTIONS THROUGH MICRORNAS

RELATED APPLICATIONS

The present application claims priority under 35 U.S.C. §119(e) to U.S. Provisional Application No. 61/382,429, filed Sep. 13, 2010, which is herein expressly incorporated by reference.

STATEMENT REGARDING FEDERALLY SPONSORED R&D

The U.S. Government has certain rights in this invention pursuant to Grant Nos. AI079243, HL102228, CA133521 awarded by the National Institutes of Health.

REFERENCE TO SEQUENCE LISTING

The present application is being filed along with a Sequence Listing in electronic format. The Sequence Listing is provided as a file entitled SEQLISTING.TXT, created Sep. 13, 2011, which is 12 Kb in size. The information in the electronic format of the Sequence Listing is incorporated herein by reference in its entirety.

BACKGROUND

1. Field of the Invention

The present disclosure relates to modulating the function of hematopoietic stem cells using microRNAs. For example, hematopoietic output, such as blood output, hematopoietic engraftment, and development and progression of cancers of immunological origin can be modulated through microRNAs that are enriched in hematopoietic stem cells, such as miR-125b, miR-126 and miR-155.

2. Description of the Related Art

MicroRNAs (miRNAs) are a recently discovered class of small RNA molecules that are emerging as potent regulators of multiple aspects of cellular function. mRNAs are an evolutionally conserved class of small RNAs involved in post-transcriptional gene repression. See, e.g., Bartel, Cell 116, 281-97 (2004); Ambros, Nature 431, 350-5 (2004); Farh et al., Science 310, 1817-21 (2005). In animals, miRNAs are processed from larger primary transcripts (pri-miRNA or pri-miR) through an approximate 60-bp hairpin precursor (pre-miRNA or pre-miR) into the mature forms (miRNA) by two RNAse III enzymes Drosha and Dicer. See, e.g., Gregory et al., Nature 432, 235-40 (2004); Chendrimada et al., Nature 436, 740-4 (2005). The mature miRNA is loaded into the ribonucleoprotein complex (RISC), where it typically guides the downregulation of target mRNA through base pair interactions. Pri-miRNAs are transcribed by RNA polymerase II and predicted to be regulated by transcription factors in an inducible manner. Lee et al., Embo J 23, 4051-60 (2004); Fazi et al., Cell 123, 819-31 (2005); O'Donnell, et al., Nature 435, 839-43 (2005). While some miRNAs show ubiquitous expression, others exhibit only limited developmental stage-, tissue- or cell type-specific patterns of expression. See, e.g., Pasquinelli, Curr. Opin. Genet. Dev. 15, 200-5 (2005). In mammals, miRNAs have been associated with diverse biological processes, such as cell differentiation (Chen, Science 303, 83-6 (2004); Monticelli, et al. Genome Biol. 6, R71 (2005); Esau, et al., J. Biol. Chem. 279, 52361-5 (2004)), cancer (Calin, et al., Proc. Natl. Acad. Sci. USA 101, 2999-3004 (2004); Lu, J. et al., Nature 435, 834-8 (2005); He, L. et al., Nature 435, 828-33 (2005)), regulation of insulin secretion (Poy et al., Nature 432, 226-30 (2004)), and viral infection (Lecellier et al., Science 308, 557-60 (2005); Sullivan and Ganem, Mol Cell 20, 3-7 (2005)). Studies in plants have shown that miRNAs can be involved in the responses to a variety of environmental stresses.

Production of blood cells depends on proper hematopoietic stem-cell (HSC) function, which involves a delicate balance between HSC self-renewal and differentiation into progenitor populations. Several reports have found that miRNAs regulate the development of some hematopoietic lineages. O'Connell et al. Nat. Rev. Immunol. 10:111-122 (2010).

SUMMARY

Some embodiments disclosed herein include a method for increasing blood output in a mammal, comprising administering a microRNA (miRNA) oligonucleotide to hematopoietic stem cells (HSCs) in the mammal. In some embodiments, the miRNA is selected from the group consisting of microRNA-125b (miR-125b), microRNA-126 (miR-126), microRNA-155 (miR-155), and a mixture thereof.

In some embodiments, the miR-125b oligonucleotide is selected from the group consisting of a mature miR-125b1 oligonucleotide, a mature miR-125b2 oligonucleotide, a pre-miR-125b1 oligonucleotide, a pre-miR-125b2 oligonucleotide, and a miR-125 seed sequence. In some embodiments, the miR-125b oligonucleotide comprises a nucleic acid sequence encoding a miR-125b selected from the group consisting of SEQ ID NOs: 1-7.

In some embodiments, administering the miR-125b oligonucleotide to the HSCs comprises contacting the HSCs with an expression construct comprising a nucleic acid encoding the miR-125b oligonucleotide, thereby the miR-125b is expressed in the HSCs.

In some embodiments, the method further comprises measuring production of blood cells in the mammal. In some embodiments, the blood cells are selected from the group consisting of red blood cells, white blood cells, platelets, and any combination thereof. In some embodiments, measuring production of blood cells comprises measuring the number of the peripheral blood cells in the mammal.

In some embodiments, the mammal suffers from low blood counts. In some embodiments, the mammal suffers from a disease or disorder selected from the group consisting of myelosuppression, pancytopenia, anemia, thrombocytopenia, leucopenia, neutropenia, and granulocytopenia.

Some embodiments disclosed herein include a method for promoting hematopoietic stem cell engraftment in a mammal in need thereof, comprising administering a microRNA-125b (miR-125b) oligonucleotide to hematopoietic stem cells (HSCs) in the mammal; and measuring proliferation of B cells, T cells, or myeloid cells in the mammal.

In some embodiments, the mammal suffers from low blood count, bone marrow failure disorders, or hematopoietic malignancies. In some embodiments, the mammal suffers from aplastic anemia.

In some embodiments, administering the miR-125b oligonucleotide to the HSCs comprises contacting the HSCs with an expression construct comprising a nucleic acid encoding the miR-125b, thereby the miR-125b oligonucleotide is expressed in the HSCs.

In some embodiments, the miR-125b oligonucleotide comprises a nucleic acid sequence encoding a miR-125b selected from the group consisting of SEQ ID NOs: 1-7.

Some embodiments disclosed herein include a method for treating a myeloproliferative disorder in a mammal in need thereof, comprising administering an antisense microRNA- 125b (miR-125b) oligonucleotide to target cells in the mammal, thereby inhibiting proliferation of myeloid cells.

In some embodiments, the antisense miR-125b oligonucleotide comprises a nucleic acid sequence encoding an antisense miR-125b selected from the group consisting of SEQ ID NOs: 8-14.

In some embodiments, the myeloproliferative disorder is selected from the group consisting of polycythemia vera, essential thrombocytosis, myelosclerosis, and myeloid leukemia. In some embodiments, the myeloid leukemia is acute myeloid leukemia (AML) or chronic myeloid leukemia (CML).

In some embodiments, administering the antisense miR-125b oligonucleotide to the target cells comprises contacting the HSCs with an expression construct comprising a nucleic acid encoding the antisense miR-125b oligonucleotide, thereby the antisense miR-125b is expressed in the HSCs.

In some embodiments, the target cells comprise hematopoietic stem cells.

Some embodiments disclosed herein include method for reducing blood output in a mammal, comprising administering a microRNA oligonucleotide to hematopoietic stem cells (HSCs) in the mammal, wherein the microRNA is selected from the group consisting of miR-196b, miR-181c, let7e, and miR-542.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
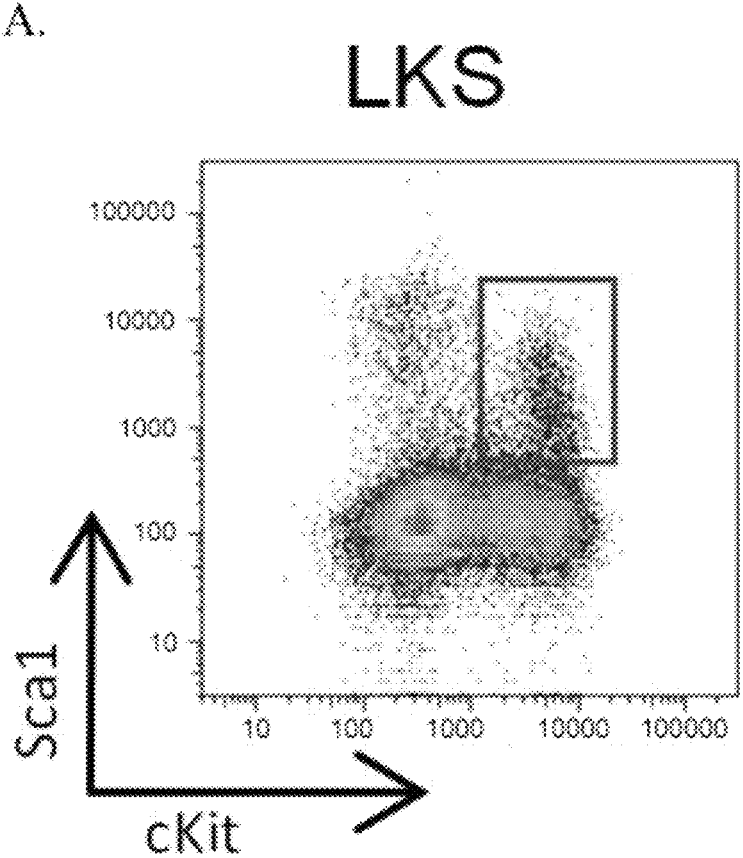
FIG. 1 shows miRNAs that are enriched in hematopoietic stem cells (HSCs). (A) Microarray analysis comparing miRNA expression in the LKS compartment (FACS plot in the upper panel and the subset box) with total bone marrow from C57BL6 mice. Number of miRNAs significantly enriched in total BM vs. the LKS compartment, unchanged between the two groups, or significantly enriched in LKS vs. total BM cells is shown in the lower panel. (B) A histogram showing enrichment of 11 miRNAs preferentially expressed in LKS cells vs. total BM determined by qPCR. (C) Expression levels of 11 miRNAs that are enriched in the LKS compartment in hematopoietic cells as compared to other bone-marrow compartments. (D) Expression levels of 11 miRNAs that are enriched in the LKS compartment in three subpopulations of LKS cells sorted by FACS according to their expression of the signaling lymphocytic activation molecule (SLAM) markers CD150 and CD48. The relative expression levels of miRNAs from each LKS subpopulation were assayed by qPCR. All data were normalized to sno202 and represent the mean+SEM.
Figure 1:
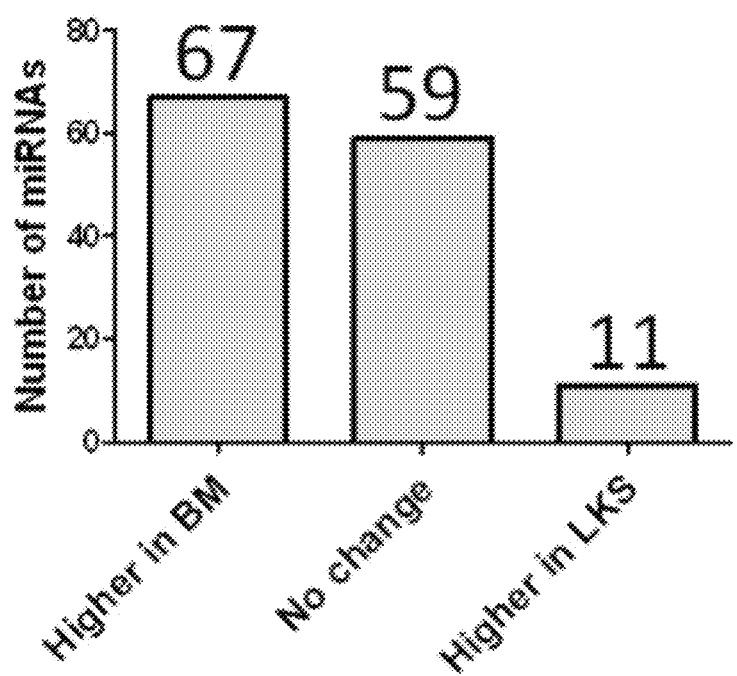
Figure 1:
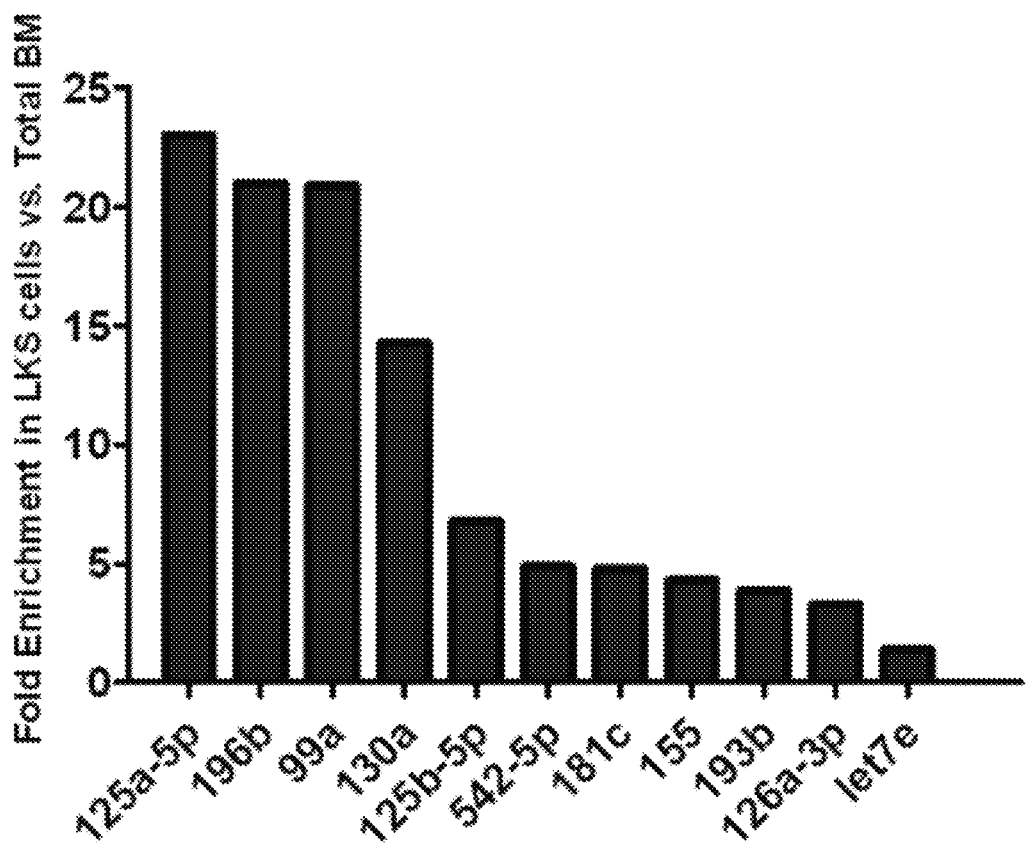
Figure 1:
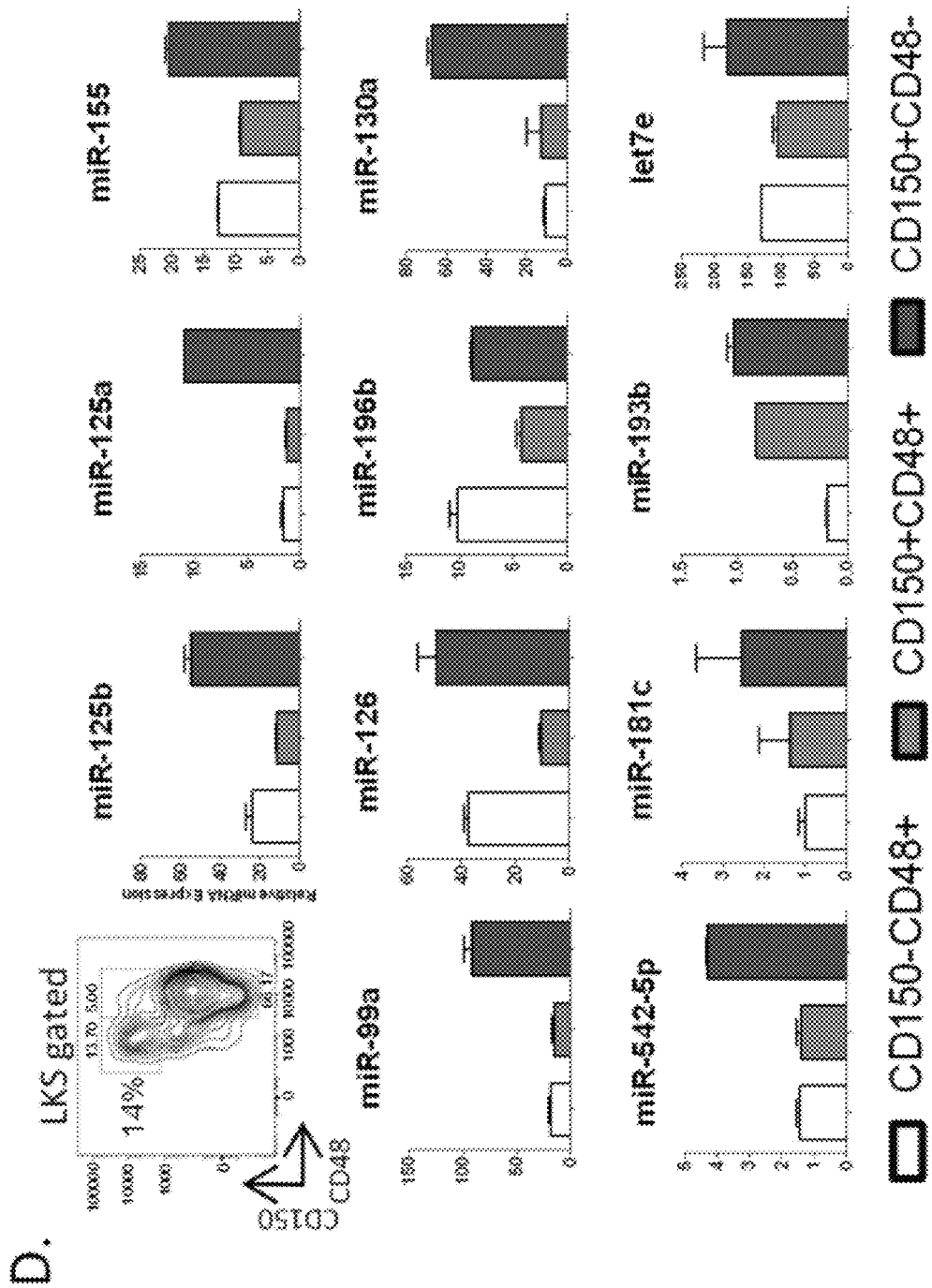

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

The present disclosure provides a number of microRNAs (miRNAs) that are enriched in hematopoietic stem cells (HSCs) as compared with other bone-marrow cells. As disclosed herein, some of these miRNAs can increase blood production, promote HSC engraftment; and some of these miRNAs can attenuate production of blood cells. The present disclosure also provides methods for treating myeloproliferative disorders, such as myeloid leukemia, using some of the miRNAs disclosed herein.

DEFINITIONS

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below.

As used herein, the terms "miR," "mir" and "miRNA" are used to refer to microRNA, a class of small non-coding RNA molecules that are capable of modulating RNA translation (see, e.g., Zeng and Cullen, RNA, 9(1):112-123 (2003); Kidner and Martienssen, Trends Genet, 19(1):13-6 (2003); Dennis C, Nature, 420(6917):732 (2002); Couzin J, Science 298 (5602):2296-7 (2002), each of which is incorporated by reference herein). The terms "miR," "mir" and "miRNA," unless otherwise indicated, include the mature, pri-, pre-form of a particular microRNA as well as the seed sequence of the microRNA and sequences comprising the seed sequence, and variants thereof. For example, the terms "mRNA-125b" and "miR-125b" are used interchangeably and, unless otherwise indicated, refer to microRNA-125b, including miR-125b, pri-miR-125b, pre-miR-125b, mature miR-125b, miRNA-125b seed sequence, sequences comprising a miRNA-125b seed sequence, and any variants thereof.

As used herein, an "expression vector" refers to a nucleic acid construct, generated recombinantly or synthetically, bearing a series of specified nucleic acid elements that enable transcription of a particular gene in a host cell. Typically, gene expression is placed under the control of certain regulatory elements, such as constitutive or inducible promoters.

As used herein, "miRNA nucleic acid" refers to a RNA or DNA that encodes a miR as defined above, or is complementary to a nucleic acid sequence encoding a miR, or hybridizes to such RNA or DNA and remains stably bound to it under appropriate stringency conditions. For example, miRNA nucleic acids include genomic DNA, cDNA, mRNA, antisense molecule, pri-miRNA, pre-miRNA, mature miRNA, miRNA seed sequence, as well as nucleic acids based on alternative backbones or including alternative bases. As used herein, miRNA nucleic acids can be derived from natural sources or synthesized.

As used herein, the terms of "microRNA seed sequence," "miRNA seed sequence," "seed region" and "seed portion" are used interchangeably, and refer to nucleotides 2-7 or 2-8 of a mature miRNA sequence. The miRNA seed sequence is typically located at the 5' end of the miRNA.

The term "operably linked" is used herein to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

As used herein, the term "variant" refers to a polynucleotide having a sequence substantially similar to a reference polynucleotide. A variant can comprises deletions, substitutions, additions of one or more nucleotides at the 5' end, 3' end, and/or one or more internal sites in comparison to the reference polynucleotide. Similarities and/or differences in sequences between variants and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variants of a particular polynucleotide disclosed herein, including, but not limited to, a miRNA, will have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans.

As used herein, "mammal" refers to an individual belonging to the class Mammalia and includes, but not limited to, humans, domestic and farm animals, zoo animals, sports and pet animals. Non-limiting examples of mammals include humans, mice, rats, sheep, dogs, horses, cats and cows. In some embodiments, the mammal is a human. However, in some embodiments, the mammal is not a human.

As used herein, "treatment" refers to a clinical intervention made in response to a disease, disorder or physiological condition manifested by a patient or to which a patient may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

As used herein, the term "effective amount" refers to an amount sufficient to effect beneficial or desirable biological and/or clinical results.

As used herein, "pharmaceutically acceptable" carriers, excipients, or stabilizers are the ones nontoxic to the cell or mammal being exposed thereto at the dosages and concentrations employed or that have an acceptable level of toxicity as determined by the skilled practitioner. In some embodiments, the physiologically acceptable carrier is an aqueous pH buffered solution. The physiologically acceptable carrier can also comprise one or more of antioxidants, such as ascorbic acid; low molecular weight polypeptides (e.g., less than about 10 residues); proteins, such as serum albumin, gelatin, and immunoglobulins; hydrophilic polymers such as polyvinylpyrrolidone; amino acids; carbohydrates such as glucose, mannose, and dextrins; chelating agents such as EDTA; sugar alcohols such as mannitol or sorbitol; salt-forming counterions such as sodium; and nonionic surfactants such as Tween™, polyethylene glycol (PEG), and Pluronics™.

As used herein, "blood output" refers to the production of blood cells in a subject (e.g., a mammal) through differentiation of cell of hematopoietic origin. In some embodiments, increasing blood output comprises promoting differentiation of hematopoietic stem cells and/or hematopoietic multipotent progenitor cells into blood cells. In some embodiments, increasing blood output comprises increasing the number of blood cells in the subject. Non-limiting examples of blood cells include red blood cells, white blood cells, platelets, and any combination thereof. In some embodiments, increasing blood output comprises increasing the number of red blood cells. In some embodiments, increasing blood output comprises increasing the number of white blood cells. In some embodiments, increasing blood output comprises increasing the number of platelets.

ABBREVIATIONS

HSCs: hematopoietic stem cells
LKS cells: lineage-negative (lin−) cKit+Sca1+ cells
BM: bone marrow
RBC: red blood cell
WBC: white blood cell
i.v.: intravenous MicroRNA Nucleic Acid Molecules MicroRNA is a class of small non-coding RNA molecules that are capable of modulating RNA translation. Mature miR-NAs are typically around 17-25 nucleotides in length, but may be longer or shorter. In nature, miRNAs are generated in cells from miRNA precursors as the result of a series of RNA processing steps. A pri-miRNA transcript having a hairpin structure is first produced. The mature miRNA is located within one arm/strand of this precursor hairpin (the opposite strand of the hairpin, known as the star(*) strand, is generally degraded (see Wang et al., 2008, Dev. Cell, 15, p 261-271)). The pri-miRNA is then processed in the nucleus to form a pre-miRNA which is exported to the cytoplasm. The pre-miRNA undergoes further processing in the cytoplasm to form the mature miRNA. It is in general the mature miRNA that inhibits expression of its target gene at the post-transcriptional level by binding to the mRNA of the target gene by Watson-Crick base pairing. MicroRNAs have been found to have roles in a variety of biological processes including developmental timing, differentiation, apoptosis, cell proliferation, organ development, and metabolism.

As disclosed above, the term "microRNA" used herein refers to the mature, pri-, and pre-form of a microRNA as well as the seed sequence of the microRNA and sequences comprising the seed sequence, and variants thereof. For example, the terms "miRNA-125b" and "miR-125b" are used interchangeably and, unless otherwise indicated, refer to microRNA-125b, including pri-miR-125b, pre-miR-125b, mature miR-125b, miRNA-125b seed sequence, sequences comprising a miRNA-125b seed sequence, and any variants thereof.

As disclosed herein, a miRNA sequence may comprise from about 6 to about 99 or more nucleotides. In some embodiments, a miRNA sequence comprises about the first 6 to about the first 24 nucleotides of a pre-miRNA-125b1 or a pre-miRNA-125b2, about the first 8 to about the first 22 nucleotides of a pre-miRNA-125b1 or a pre-miRNA-125b2, or about the first 10 to about the first 20 nucleotides of a pre-miRNA-125b1 or a pre-miRNA-125b2. In some embodiments, the miRNA can be an isolated or purified oligonucleotide having at least 6, 7, 8, 10, 11, 12, 13, 14, 15, 16, 17, 18, 19, 20, 21, 22, 23, 24, or 25 nucleotides in length. In some embodiments, the miRNA is a hybridizable portion of a miR-125b coding sequence or its complementary sequence. In some embodiments, the miRNA oligonucleotide has at least 10, 11, 12, 13, 14, 15, 16, 17, 18, 19, 20, 21, 22, 23, 24, or 25 nucleotides. In some embodiments, the miR-125b oligonucleotide has at least 19, 20, 21, 22, 23, 24, or 25 nucleotides.

It is not intended that the methods disclosed herein be limited by the source of the microRNA. As disclosed herein, the microRNAs can be naturally-occurring or synthetic. In some embodiments, the microRNA can effectively reduce the expression of target polynucleotides through RNA interference. In some embodiments, a synthetic miRNA can have a sequence that is different from a naturally-occurring miRNA and effectively mimic the naturally-occurring miRNA. For example, the synthetic miRNA can have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or greater sequence similarity to the naturally-occurring miRNA. In some embodiments, the microRNA can be a naturally-occurring or synthetic miR-125b1 or miR-125b2. In some embodiments, the microRNA can be a human or mouse miR-125b1 or miR-125b2. In some embodiments, the microRNA can be a naturally-occurring or synthetic miR-126. In some embodiments, the microRNA can be a human or mouse miR-126. In some embodiments, the microRNA can be a naturally-occurring or synthetic miR-155. In some embodiments, the microRNA can be a human or mouse miR-155. For example, miRNA precursors can be purchased from Ambion®.

The mature microRNA may be generated from various precursors, including but not limited to, a primary microRNA transcript (pri-miRNA), a hairpin RNA comprising a miRNA that has been introduced into a cell (including shRNA molecules), or a transcript comprising a microRNA that has been encoded by plasmid DNA that has been introduced into a cell.

Inhibition of Micro-RNAs

The present disclosure provides inhibitors of miRNAs (i.e., anti-miRNA), for example the inhibitors for the HSC-enriched miRNAs disclosed herein. Compositions comprising such inhibitors and methods for inhibiting miRNAs using such inhibitors are also disclosed herein. Any miRNA inhibitor may be used alone, or with other miRNA inhibitor(s) known in the art. In some embodiments, the miRNA inhibitor is a nucleic acid-based inhibitor that is capable of forming a duplex with the target miRNA by Watson-Crick type base pairing. One of the non-limiting examples of the nucleic acid-based miRNA inhibitor is an antisense oligonucleotide.

It is not necessary that there be perfect complementarity between the nucleic acid-based miRNA inhibitor and the target miRNA. The miRNA inhibitor may have one or more regions of non-complementarity with the target miRNA flanked by one or more regions of complementarity sufficient to allow duplex formation. In some embodiments, the regions of complementarity can be at least 6, 7, 8, 9, 10, 11, 12, 13, 14, 15, 16, 17, 18, 19, 20, 21, 22, 23, 24, or 25 nucleotides long.

As used herein, the mechanism by which the miRNA inhibitor functions to inhibit the activity of the target miRNA is not limited in any way. For example, a nucleic acid-based inhibitor, in some embodiments, may form a duplex with the target miRNA sequences and prevent proper processing of the mature miRNA product from its precursor, or may prevent the mature miRNA from binding to its target gene, or may lead to degradation of pr-, pre-, or mature miRNA, or may act through some other mechanism.

In some embodiments, a miRNA inhibitor (for example, an inhibitor for miR-125b, miR-126, or miR-155) is used to attenuate, reduce, block, or abolish the activity of the target miRNA. The extent to which the activity of the miRNA is reduced can vary. For example, the miRNA inhibitors disclosed herein can reduce the activity of the target miRNA by at least about 10%, at least about 20%, at least about 30%, at least about 40%, at least about 50%, at least about 60%, at least about 70%, at least about 80%, at least about 90%, at least about 95%, at least about 98%, or at least about 99%. In some embodiments, the miRNA inhibitor can completely abolish the activity of the target miRNA. Non-limiting examples of miRNA inhibitors include nucleic acids that can block the activity of a miRNA, such as an antisense miRNA. Such nucleic acids include, for example, antisense miR-125b1 oligonucleotide and antisense miR-125b2 oligonucleotide; antisense miR-126 oligonucleotide; and antisense miR-155 oligonucleotide. In some embodiments, the anti-miRNA can have a total of at least about 5 to about 26 nucleotides. In some embodiments, the sequence of the anti-miRNA can have at least 5, 6, 7, 8, 9, 10, 11, 12, 13, 14, 15, 16, 17, 18, 19, 20, or 21 nucleotides that are substantially complementary to the 5' region of a miR-125b1, a miR-125b2, a miR-126 or a miR-155; at least 5, 6, 7, 8, 9, 10, 11, 12, 13, 14, 15, 16, 17, 18, 19, 20, or 21 nucleotides that are substantially complementary to the 3' region of a miR-125b, a miR-126 or a miR-155. In some embodiments, the sequence of the anti-miRNA can comprise at least 4-7 nucleotides that are substantially complementary to a miR-125b seed sequence, a miR-126 seed sequence, or a miR-155 seed sequence. In some embodiments, the sequence of the anti-miRNA can comprise at least 5-12 nucleotide that are substantially complementary to the flanking regions of a miR-125b seed sequence, a miR-126 seed sequence or a miR-155 seed sequence. In some embodiments, the anti-miRNA is an antisense miR-125b nucleic acid comprising a total of about 5 to about 100 or more nucleotides, more preferably about 10 to about 60 nucleotides or about 15 to about 30 nucleotides, and has a sequence that is preferably complementary to at least the seed region of miR-125b. In some embodiments, the anti-miRNA is an antisense miR-126 nucleic acid comprising a total of about 5 to about 100 or more nucleotides, more preferably about 10 to about 60 nucleotides or about 15 to about 30 nucleotides, and has a sequence that is preferably complementary to at least the seed region of miR-126. In some embodiments, the anti-miRNA is an antisense miR-155 nucleic acid comprising a total of about 5 to about 100 or more nucleotides, more preferably about 10 to about 60 nucleotides or about 15 to about 30 nucleotides, and has a sequence that is preferably complementary to at least the seed region of miR-155. It has been shown that antisense miRNAs can specifically silence target miRNA in tissue. Krutzfeldt, J. et al., Nature, 438:685-9 (2005).

As disclosed herein, the miRNA or anti-sense miRNA oligonucleotide can be from a human or non-human mammal, derived from any recombinant source, synthesized in vitro or by chemical synthesis. The oligonucleotide can be DNA or RNA, and can in a double-stranded, single-stranded or partially double-stranded form. The miRNA oligonucleotides (e.g., miR-125b and anti-miR-125b oligonucleotides) can be prepared by any conventional means known in the art to prepare nucleic acids. For example, nucleic acids may be chemically synthesized using commercially available reagents and synthesizers by methods that are well-known in the art, including, but not limited to, the phosphotriester method described in Matteucci, et al., (J. Am. Chem. Soc. 103:3185-3191, 1981) and/or an automated synthesis method described in Gait (Oligonucleotide Synthesis: A Practical Approach, 1985, IRL Press, Oxford, England). Larger DNA or RNA segments can also readily be prepared by conventional methods known in the art, such as synthesis of a group of oligonucleotides that define various modular segments, followed by ligation of oligonucleotides to build the complete segment.

The miRNA inhibitor can comprise modified or unmodified nucleotides. In some embodiments, modified nucleotides or backbone modifications can be used to increase stability and/or optimize delivery of the sense or antisense oligonucleotides. Non-limiting modified nucleotides include linked nuclear acid (LNA), 2'-O-Me nucleotides, 2'-O-methoxyethyl, and 2' fluoro. Backbone modifications include, but are not limited to, phosphorothioate and phosphate. In some embodiments, a microRNA or an antisense microRNA oligonucleotide disclosed herein (e.g., miR-125b or anti-miR-125b oligonucleotide) can be modified with cholesterol to enhance delivery to target cells. The cholesterol can be linked, for example, through a hydroxyprolinol linkage on the 3' end of the microRNA.

In some embodiments, the miRNA inhibitor can comprise ribonucleotides, deoxyribonucleotides, 2'-modified nucleotides, phosphorothioate-linked deoxyribonucleotides, peptide nucleic acids (PNAs), locked nucleic acids (LNAs), or other forms of naturally or non-naturally occurring nucleotides. The miRNA inhibitor can comprise nucleobase modifications, include, but not limited to, 2-amino-A, 2-thio (e.g., 2-thio-U), G-clamp modifications, antagomirs, morpholinos, nucleic acid aptamers, or any other type of modified nucleotide or nucleotide derivative that is capable of Watson-Crick type base pairing with a miRNA. As an example, in addition to naturally occurring DNA and/or RNA nucleotide bases, non-naturally occurring modified nucleotide bases that can be used in the miRNA inhibitors disclose herein, include, but are not limited to, 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carb 1 pseudouridine, beta-D-galactosylqueosine, 2'-Omethylguanosine, inosine, $N^6$-isopente nyladenosine, 1-methyladenosine, 1-methylpseudouridine, 1-methylguanosine, 1-methylaminomethyllinosine, 2,2-dimethylguanosine, 2-methyladenosine, 2-methylguanosine, 3-methylcytidine, 5-methylcytidine, N.sup.6-methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-(3-amino-3-carboxypropyl) uridine. In some embodiments, the miRNA inhibitor comprises morpholinos or antagomirs.

The miRNA inhibitors disclosed herein can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. A 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

The 5'-terminus of the miRNA inhibitors disclosed herein can also be blocked with an aminoalkyl group, e.g., a 5'-O-alkylamino substituent. Other 5' conjugates can inhibit 5'-3' exonucleolytic cleavage. A 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

The miRNA inhibitors disclosed herein can also be attached to a peptide or a peptidomimetic ligand which may affect pharmacokinetic distribution of the miRNA inhibitor such as by enhancing cellular recognition, absorption and/or cell permeation. The peptide or peptidomimetic moiety can be about 5-50 amino acids long, e.g., about 5, 10, 15, 20, 25, 30, 35, 40, 45, or 50 amino acids long. A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724 (2003)).

MiR-125b Nucleic Acid Molecules

Mir-125b is expressed from two loci in both the mouse and human genomes, and these sequences are referred to as miR-125b1 and miR-125b2. In mouse genome, miR-125b1 and miR-125b2 sequences are located on chromosome 9 and 16, respectively. In human genome, miR-125b1 and miR-125b2 sequences are located on chromosome 11 and 21, respectively. miR-125b is overexpressed in certain types of acute myeloid leukemia (AML). Klusmann et al., Genes Dev 24:478-490 (2010); Bousquet et al., J Exp Med 205:2499-2506 (2008).

Nucleic acid molecules that encode miR-125b can be used in various embodiments disclosed herein. Sequences for mature miR-125b and pre-miR-125b are provided in SEQ ID NOs: 1, 2, 3, 5 and 6 respectively. Sequences for the seed sequence of miR-125b are provided in SEQ ID NOs 4 and 7, respectively Nucleic acid molecules encoding pri-miR-125b sequences can also be used herein. As disclosed herein, the scope of the present disclosure is not limited to naturally occurring miR-125b sequences; mutants and variants of miR-125b sequences are also covered by the scope of the current disclosure.

In some embodiments, an anti-miR-125b comprises the complement of a sequence of a miRNA referred to in SEQ ID NOs: 8, 9, 10, 11, 12, 13 and 14. In some embodiments, the anti-miR-125b comprises the complement of the seed sequence of SEQ ID NO: 4 or 7, or is able to hybridize under stringent conditions to the miRNA-125b seed sequence of SEQ ID NO: 4 or 7. Preferred anti-miR-125b molecules are those that are able to hybridize under stringent conditions to the complement of a cDNA encoding a mature miR-125b, for example SEQ ID NO: 8 or SEQ ID NO: 9. Non-limiting examples of antisense miR-125b1 and miR-125b2 sequences are provide in SEQ ID NOs: 8, 9, 10, 11, 12, 13, and 14.

MiR-126 and MiR-155 Nucleic Acid Molecules

Nucleic acid molecules that encode miR-126 and miR-155 can be used in various embodiments disclosed herein. Sequences for mature miR-126 and pre-miR-126 are provided in SEQ ID NOs: 15, 16, 17, 24, 25, and 27, respectively. Sequences for the seed sequence of miR-126 are provided in SEQ ID NOs 18, 19, 26 and 28, respectively Nucleic acid molecules encoding pri-miR-126 sequences can also be used herein. As disclosed herein, the scope of the present disclosure is not limited to naturally occurring miR-126 sequences; mutants and variants of miR-126 sequences are also covered by the scope of the current disclosure.

In some embodiments, an anti-miR-126 comprises the complement of a sequence of a miRNA referred to in SEQ ID NOs: 15, 16, 17, 24, 25, and 27. In some embodiments, the anti-miR-126 comprises the complement of the seed sequence of SEQ ID NO: 18, 19, 26, or 28, or is able to hybridize under stringent conditions to the miRNA-125b seed sequence of SEQ ID NO: 18, 19, 26, or 28. Non-limiting examples of antisense miR-126 sequences are provided in SEQ ID NOs: 20, 21, 22, and 23.

Sequences for mature miR-155 and pre-miR-155 are provided in SEQ ID NOs: 29, 30, 33, and 34, respectively. Sequences for the seed sequence of miR-155 are provided in SEQ ID NOs 31 and 35, respectively. Nucleic acid molecules encoding pri-miR-155 sequences can also be used herein. As disclosed herein, the scope of the present disclosure is not limited to naturally occurring miR-155 sequences; mutants and variants of miR-155 sequences are also covered by the scope of the current disclosure.

In some embodiments, an anti-miR-155 comprises the complement of a sequence of a miRNA referred to in SEQ ID NOs: 29, 30, 31, 33, 34, and 35. In some embodiments, the anti-miR-155 comprises the complement of the seed sequence of SEQ ID NO: 31 or 35, or is able to hybridize under stringent conditions to the miR-155 seed sequence of SEQ ID NO: 31 or 35. A non-limiting example of antisense miR-155 sequences is provided in SEQ ID NOs: 32.

MiR-196b, MiR-181c, Let7e, and MiR-542 Nucleic Acid Molecules

Nucleic acid molecules that encode miR-196b, miR-181c, let7e and miR-542 can be used in various embodiments disclosed herein.

Sequences for mature and pre-miR-196b are provided in SEQ ID NOs: 36, 37, 38, 39, 40, and 41, respectively. Nucleic acid molecules encoding pri-miR-196b sequences can also be used herein. As disclosed herein, the scope of the present disclosure is not limited to naturally occurring miR-196b sequences; mutants and variants of miR-196b sequences are also covered by the scope of the current disclosure. In some embodiments, an anti-miR-196b comprises the complement of a sequence of a miRNA referred to in SEQ ID NOs: 36, 37, 38, 39, 40, and 41. In some embodiments, the anti-miR-196b comprises the complement of the sequence of SEQ ID NO: 36, 37, 38, 39, 40, or 41, or is able to hybridize under stringent conditions to the miRNA-196b sequence of SEQ ID NO: 36, 37, 38, 39, 40, or 41.

Sequences for mature and pre-miR-181c are provided in SEQ ID NOs: 42, 43, 44, 45, 46, and 47, respectively. Nucleic acid molecules encoding pri-miR-181c sequences can also be used herein. As disclosed herein, the scope of the present disclosure is not limited to naturally occurring miR-181c sequences; mutants and variants of miR-181c sequences are also covered by the scope of the current disclosure. In some embodiments, an anti-miR-181c comprises the complement of a sequence of a miRNA referred to in SEQ ID NOs: 42, 43, 44, 45, 46, and 47. In some embodiments, the anti-miR-181c comprises the complement of the sequence of SEQ ID NO: 42, 43, 44, 45, 46, or 47, or is able to hybridize under stringent conditions to the miRNA-181c sequence of SEQ ID NO: 42, 43, 44, 45, 46, or 47.

Sequences for mature and pre-let7e are provided in SEQ ID NOs: 48, 49, 50, 51, 52, and 53, respectively. Nucleic acid molecules encoding pri-let7e sequences can also be used herein. As disclosed herein, the scope of the present disclosure is not limited to naturally occurring let7e sequences; mutants and variants of let7e sequences are also covered by the scope of the current disclosure. In some embodiments, an anti-let7e comprises the complement of a sequence of a miRNA referred to in SEQ ID NOs: 48, 49, 50, 51, 52, and 53. In some embodiments, the anti-let7e comprises the complement of the sequence of SEQ ID NO: 48, 49, 50, 51, 52, or 53, or is able to hybridize under stringent conditions to the let7e sequence of SEQ ID NO: 48, 49, 50, 51, 52, or 53.

Sequences for mature and pre-miR-542 are provided in SEQ ID NOs: 54, 55, 56, 57, 58, and 59, respectively. Nucleic acid molecules encoding pri-miR-542 sequences can also be used herein. As disclosed herein, the scope of the present disclosure is not limited to naturally occurring miR-542 sequences; mutants and variants of miR-542 sequences are also covered by the scope of the current disclosure. In some embodiments, an anti-miR-542 comprises the complement of a sequence of a miRNA referred to in SEQ ID NOs: 54, 55, 56, 57, 58, and 59. In some embodiments, the anti-miR-542 comprises the complement of the sequence of SEQ ID NO: 54, 55, 56, 57, 58, or 59, or is able to hybridize under stringent conditions to the miR-542 sequence of SEQ ID NO: 54, 55, 56, 57, 58, or 59.

MicroRNA Expression Constructs

In some embodiments, expression constructs that comprise an expression vector and a coding sequence for miRNA or anti-miRNA inserted thereof can be used to deliver the miRNA or anti-miRNA to a target cell (e.g., a eukaryotic ells, a mammalian cell, and a mammalian HSC). In addition to the miRNA or anti-miRNA coding sequence, the expression construct may contain one or more additional components, including, but not limited to regulatory elements. Non-limiting examples of the regulatory elements include promoter, enhancer, and other regulatory elements. In some embodiments, the miRNA or anti-miRNA coding sequence is optionally associated with a regulatory element that directs the expression of the coding sequence in a target cell.

It will be appreciated by skilled artisans that the choice of expression vectors and/or regulatory elements to which the miRNA or anti-miRNA encoding sequence is operably linked generally depends on the functional properties desired, e.g., miRNA transcription, and the host cell to be transformed. Examples of expression regulatory elements include, but are not limited to, inducible promoters, constitutive promoters, enhancers, and other regulatory elements. In some embodiments, the miRNA or anti-miRNA (e.g., miR-125b or anti-miR-125b) coding sequence is operably linked with an inducible promoter. In some embodiments, the promoter is an elongation factor 1α (EF1α) promoter, a U6 promoter, or a CMV promoter.

In some embodiments, the expression vector can replicate and direct expression of a miRNA or anti-miRNA (e.g., miR-125b or anti-miR-125b) in the target cell. Various expression vectors that can be used herein include, but are not limited to, expression vectors that can be used for nucleic acid expression in prokaryotic and/or eukaryotic cells. Non-limiting examples of expression vectors for use in prokaryotic cells include pUC8, pUC9, pBR322 and pBR329 available from BioRad Laboratories, (Richmond, Calif.), pPL and pKK223 available from Pharmacia (Piscataway, N.J.). Non-limiting examples of expression vectors for use in eukaryotic cells include pSVL and pKSV-10 available from Pharmacia; pBPV-1/pML2d (International Biotechnologies, Inc.); pcDNA and pTDT1 (ATCC, #31255); viral vectors based on vaccinia virus, poliovirus, adenovirus, adeno-associated virus, herpes simplex virus, a lentivirus; vectors derived from retroviruses such as Rous Sarcoma Virus, Harvey Sarcoma Virus, avian leukosis virus, human immunodeficiency virus, myeloproliferative sarcoma virus, and mammary tumor virus); and the like. Additional examples of suitable eukaryotic vectors include bovine papilloma virus-based vectors, Epstein-Barr virus-based vectors, SV40, 2-micron circle, pcDNA3.1, pcDNA3.1/GS, pYES2/GS, pMT, p IND, pIND (Sp1), pVgRXR (Invitrogen), and the like, or their derivatives.

In some embodiments, the expression construct integrates into the genome of the host cell (e.g., a HSC). In some embodiments, the expression construct is maintained extra-chromosomally in the host cell comprising the expression construct. A host cell (e.g., an HSC) comprising a subject recombinant vector is referred to as a "genetically modified" host cell herein.

In some embodiments, the expression vectors disclosed herein can include one or more coding regions that encode a polypeptide (a "marker") that allows for detection and/or selection of the genetically modified host cell comprising the expression vectors. The marker can be a drug resistance protein such as neomycin phosphotransferase, aminoglycoside phosphotranferase (APH); a toxin; or fluorescence. Various selection systems that are well known in the art can be used herein. The selectable marker can optionally be present on a separate plasmid and introduced by co-transfection.

Skilled artisans will appreciate that any methods, expression vectors, and target cells suitable for adaptation to the expression of a miRNA or anti-miRNA in target cells can be used herein and can be readily adapted to the specific circumstances.

Delivery of MicroRNA Oligonucleotides and Expression Constructs to a Target Cell or a Tissue In some embodiments, the miRNA or the anti-miRNA oligonucleotide is delivered to a target cell. In some embodiments, an expression construct encoding the miRNA or the anti-miRNA is delivered to a target cell where the miRNA or anti-miRNA is expressed. Methods for delivery of oligonucleotides and expression constructs to target cells are known in the art and non-limiting exemplary methods are described briefly below. Target cells can be, for example, any stem or progenitor cells, such as HSCs or hematopoietic multi-potent progenitor cells. Target cells may be present in a host, such as in a mammal; or may be in culture outside of a host. In some embodiments, the miRNA or the anti-miRNA (e.g., miR-125b or anti-miR-125b) oligonucleotide is delivered to the target cell in vivo. In some embodiments, the miRNA or the anti-miRNA (e.g., miR-125b or anti-miR- 125b) oligonucleotide is delivered to the target cell ex vivo. In some embodiments, the miRNA or the anti-miRNA (e.g., miR-125b or anti-miR-125b) oligonucleotide is delivered to the target cell in vitro.

In some embodiments, the miRNA or the anti-miRNA oligonucleotide (e.g., the miR-125b or anti-miR-125b oligonucleotide) is delivered to a target organ or tissue. Non-limiting examples of target organs and tissues include organs and tissues where hematopoietic and/or immune cells or precursors of such cells are known to be located and may include, for example and without limitation, the peritoneal cavity, spleen, lymph nodes, including mesenteric lymph nodes and peripheral lymph nodes, thymus, and bone marrow.

Delivery of oligonucleotides and/or expression constructs to a target cell can be achieved in a variety of ways. In some embodiments, a transfection agent is used. As used herein, the terms "transfection agent," "transfection reagent" and "delivery vehicle," are used interchangeable and refer to a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, polycations, histone proteins, polyethylenimine, polylysine, and polyampholyte complexes. One example of transfection reagent suitable for delivery of miRNA is siPORT™ NeoFX™ Transfection Agent (Ambion, Inc.), which can be used to transfect a variety of cell types with miRNA. miRNAs can be readily electroporated into primary cells without inducing significant cell death. miRNAs can be transfected at various concentrations. The transfection efficiency of synthetic miRNAs has been shown to be very good, and around 100% for certain cell types (Ambion, Inc. miRNA Research Guide, page 12).

Examples of reagents for delivery of miRNA, anti-miRNA and expression constructs include, but are not limited to, protein and polymer complexes (polyplexes), lipids and liposomes (lipoplexes), combinations of polymers and lipids (lipopolyplexes), and multilayered and recharged particles. Transfection agents may be used to condense nucleic acids. Transfection agents may also be used to associate functional groups with a polynucleotide. Non-limiting examples of functional groups include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers). For delivery in vivo, complexes made with sub-neutralizing amounts of cationic transfection agent can be used.

In some embodiments, polycations are mixed with the miRNA or the anti-miRNA oligonucleotide disclosed herein for delivery to a target cell. In some embodiments, the miRNA or the anti-miRNA oligonucleotide and one or more transfection reagents are delivered systematically such as by injection. In some embodiments, the miRNA or the anti-miRNA oligonucleotide can be injected into particular areas comprising target cells, such as particular organs, for example the bone marrow.

In some embodiments, the miRNA, anti-miRNA or expression construct can be delivered systemically. In some embodiments, the miRNA, anti-miRNA or expression construct can be delivered in combination with one or more pharmaceutically acceptable carriers. In some embodiments, the miRNA, anti-miRNA or expression construct can be injected intravenously.

Polymer reagents for delivery of the miRNA, anti-miRNA and expression vectors may incorporate compounds that increase their utility. These groups can be incorporated into monomers prior to polymer formation or attached to polymers after their formation. A vector transfer enhancing moiety is typically a molecule that modifies a nucleic acid complex and can direct it to a cell location (such as tissue cells) or location in a cell (such as the nucleus) either in culture or in a whole organism. By modifying the cellular or tissue location of the complex, the desired localization and activity of the miRNA, anti-miRNA or expression vector can be enhanced. The transfer enhancing moiety can be, for example, a protein, a peptide, a lipid, a steroid, a sugar, a carbohydrate, a nucleic acid, a cell receptor ligand, or a synthetic compound. The transfer enhancing moieties can, in some embodiments, enhance cellular binding to receptors, cytoplasmic transport to the nucleus and nuclear entry or release from endosomes or other intracellular vesicles.

Nuclear localizing signals (NLSs) can also be used to enhance the targeting of the miRNA, anti-miRNA or expression vector into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors such as the NLS receptor (karyopherin alpha) which then interacts with karyopherin beta. The nuclear transport proteins themselves can also, in some embodiments, function as NLS since they are targeted to the nuclear pore and nucleus.

Compounds that can cause or enhance release of nucleic acids from intracellular compartments such as endosomes (early and late), lysosomes, phagosomes, vesicle, endoplasmic reticulum, Golgi apparatus, trans Golgi network (TGN), and sarcoplasmic reticulum can be used to aid delivery of the miRNA or anti-miRNA (e.g., miRNA-125b or anti-miR-125b). The release includes movement out of an intracellular compartment into cytoplasm or into an organelle such as the nucleus. Examples of such compounds include, but are not limited to, chemical compounds such as chloroquine, bafilomycin, Brefeldin A1; ER-retaining signal (KDEL sequence); viral components such as influenza virus hemagglutinin subunit HA-2 peptides; and other types of amphipathic peptides.

Cellular receptor moieties are any signal that enhances association of the miRNA, anti-miRNA or expression vector with a cell. Enhanced cellular association can be accomplished by either increasing the binding of miRNAs, anti-mRNAs, or expression constructs encoding miRNA or anti-miRNA to the cell surface and/or their association with an intracellular compartment. For example, enhanced cellular association can be achieved by ligands that enhance endocytosis. Cellular receptor moieties include agents that target to asialoglycoprotein receptors by using asialoglycoproteins or galactose residues. Viral proteins, proteins such as insulin, EGF, or transferring; peptides that include the RGD sequence; chemical groups that react with sulfhydryl or disulfide groups on cells; folate and other vitamins can also be used for targeting. Other non-limiting targeting groups include molecules that interact with membranes such as lipids fatty acids, cholesterol, dansyl compounds, and amphotericin derivatives.

Skilled artisans will be able to select and use an appropriate system for delivering the miRNA or anti-miRNA or an expression vector to target cells in vitro, ex vivo, or in vivo without undue experimentation.

Modulation of HSC Function and/or Proliferation

Some of the miRNAs disclosed herein can be used to modulate function, activity and/or proliferation of HSCs.

Proliferation, function, and activity of HSCs can be modulated by administering an oligonucleotide of miRNA or anti-miRNA (e.g., antisense miRNA) to HSCs. The target cells can be in a mammal. Various miRNA disclosed herein can be used to modulate function, activity and/or proliferation of HSCs. For example, the miRNA can be miR-125b-5p, miR-126-3p, miR-155, miR-196b, miR-181c, let7e, miR-542, and mixture thereof.

In some embodiments, the miRNA or antisense miRNA, for example, miR-125b or antisense miR-125b, is delivered to bone marrow. Variants of the microRNAs or anti-miRNA disclosed and fragments thereof can also be used in the methods disclosed herein. In some embodiments, proliferation of HSCs, myeloid cells and/or lymphoid cells can be used to measure the effects of miR-125b or anti-miR-125b, miR-126 or anti-miR126, or miR-155 or anti-miR155 is delivered to bone marrow. For example, proliferation of B cells, T cells, white blood cells, and/or red blood cells can be measured. Measurements of proliferation can take place in an appropriate spot for each cell type, such as in the bone marrow, thymus, spleen, periphery, peritoneal cavity, or lymph nodes (e.g., mesenteric lymph nodes and peripheral lymph nodes). Measurement of proliferation can be achieved by any method known in the art, for example by FACS analysis or qPCR.

In some embodiments, miR-125b or antisense miR-125b oligonucleotide can be administered by contacting target cells, for example HSCs or hematopoietic multipotent progenitor cells, with an expression contract comprising a nucleic acid encoding the miR-125b or antisense miR-125b, thereby the miR-125b or antisense miR-125b is expressed in the target cells.

In some embodiments, miR-126 or antisense miR-126 oligonucleotide can be administered by contacting target cells, for example HSCs or hematopoietic multipotent progenitor cells, with an expression contract comprising a nucleic acid encoding the miR-126 or antisense miR-126, thereby the miR-126 or antisense miR-126 is expressed in the target cells.

In some embodiments, miR-155 or antisense miR-155 oligonucleotide can be administered by contacting target cells, for example HSCs or hematopoietic multipotent progenitor cells, with an expression contract comprising a nucleic acid encoding the miR-155 or antisense miR-155, thereby the miR-126 or antisense miR-155 is expressed in the target cells.

In some embodiments, function, proliferation and/or activity of hematopoietic stem cells (HSCs) can be regulated by delivering a miRNA or an anti-miRNA to the HSCs. In some embodiments, the miRNA is miR-125b, miR-126, or miR-155. In some embodiments, function, proliferation and/or activity of hematopoietic multi-potent progenitor cells can be regulated by delivering a miRNA or an anti-miRNA to the hematopoietic multi-potent progenitor cells, wherein the miRNA is miR-125b, miR-126, or miR-155. In some embodiments, function, proliferation and/or activity of HSCs can be regulated by delivering an antisense miRNA to the HSCs, wherein the antisense miRNA is antisense miR-125b, antisense miR-126, or antisense miR-155. The function, proliferation and/or activity of HSCs and hematopoietic multi-potent progenitor cells can be either upregulated or downregulated.

In some embodiments, activity and/or proliferation of HSCs is upregulated by administering an oligonucleotide or expression construct for a HSC-enriched miRNA, such as miR-125b, miR-126 and/or miR-155, to target cells, tissues or organs. Increased number of cells of hematopoietic origin, including but not limited to B cells, T cells, WBCs and RBCs, can be detected, for example, by FACS analysis after administering an oligonucleotide or expression construct for a HSC-enriched miRNA, such as miR-125b, miR-126 or miR-155, to target cells, tissues or organs.

In some embodiments, activity and/or proliferation of HSCs is downregulated by administering an oligonucleotide or expression construct for an antisense miR-125b, an antisense miR-126 or an antisense miR-155, to target cells, tissues or organs. Decreased number of cells of hematopoietic origin, including but not limited to B cells, T cells, WBCs and RBCs, can be detected, for example, by FACS analysis after administering the antisense miR-125b, the antisense miR-126 or the antisense miR-155, to target cells, tissues or organs.

Any of the sequences of miR-125b or antisense miR-125b disclosed herein and variants thereof can be used to regulate proliferation, activity and/or function of HSCs or hematopoietic multipotent progenitor cells. In some embodiments, the miR-125b oligonucleotide comprises all or a portion of mature miR-125b, pre-miR-125b1, pre-miR-125b2, pri-miR-125b1, pri-miR-125b2, or a miR-125b seed sequence. Mixtures of various miR-125b nucleic acids can also be used. In some embodiments, the miR-125b comprises all or a portion of a sequence selected from the group consisting of SEQ ID NOs: 1, 2, 3, 4, 5, 6, and 7. In some embodiments, the miR-125b expression construct comprises a sequence encoding a miR-125b selected from the group consisting of SEQ ID NOs: 1, 2, 3, 4, 5, 6, and 7. In some embodiments, the antisense miR-125b is complementary to all or a portion of SEQ ID NOs: 1, 2, 3, 4, 5, 6, and 7. In some embodiments, the antisense miR-125b hybridizes under stringent conditions to one or more of SEQ ID NOs: 1, 2, 3, 4, 5, 6, and 7. In some embodiments, the antisense miR-125b comprises a sequence selected from the group consisting of SEQ ID NOs: 8, 9, 10, 11, 12, 13, and 14.

Any of the sequences of miR-126 or antisense miR-126 disclosed herein and variants thereof can be used to regulate proliferation, activity and/or function of HSCs or hematopoietic multipotent progenitor cells. In some embodiments, the miR-126 oligonucleotide comprises all or a portion of mature miR-126, pre-miR-126, pri-miR-126, or a miR-126 seed sequence. Mixtures of various miR-126 nucleic acids can also be used. In some embodiments, the miR-126 comprises all or a portion of a sequence selected from the group consisting of SEQ ID NOs: 15, 16, 17, 18, 19, 24, 25, 26, 27, and 28. In some embodiments, the miR-126 expression construct comprises a sequence encoding a miR-126 selected from the group consisting of SEQ ID NOs: 15, 16, 17, 18, 19, 24, 25, 26, 27, and 28. In some embodiments, the antisense miR-126 is complementary to all or a portion of SEQ ID NOs: 15, 16, 17, 18, 19, 24, 25, 26, 27, and 28. In some embodiments, the antisense miR-126 hybridizes under stringent conditions to one or more of SEQ ID NOs: 15, 16, 17, 18, 19, 24, 25, 26, 27, and 28. In some embodiments, the antisense miR-126 comprises a sequence selected from the group consisting of SEQ ID NOs: 20, 21, 22, and 23.

Any of the sequences of miR-155 or antisense miR-155 disclosed herein and variants thereof can be used to regulate proliferation, activity and/or function of HSCs or hematopoietic multipotent progenitor cells. In some embodiments, the miR-155 oligonucleotide comprises all or a portion of mature miR-155, pre-miR-155, pri-miR-155, or a miR-155 seed sequence. Mixtures of various miR-155 nucleic acids can also be used. In some embodiments, the miR-155 comprises all or a portion of a sequence selected from the group consisting of SEQ ID NOs: 29, 30, 31, 33, 34, and 35. In some embodiments, the miR-155 expression construct comprises a sequence encoding a miR-155 selected from the group consisting of SEQ ID NOs:. In some embodiments, the antisense miR-155 is complementary to all or a portion of SEQ ID NOs: 29, 30, 31, 33, 34, and 35. In some embodiments, the antisense miR-155 hybridizes under stringent conditions to one or more of SEQ ID NOs: 29, 30, 31, 33, 34, and 35. In some embodiments, the antisense miR-155 comprises a sequence of SEQ ID NO: 32.

In some embodiments, mixtures of various miR-125b, miR-126 and miR-155 nucleic acids can be used.

In some embodiments, the blood output in a subject is regulated by administering a miRNA oligonucleotide to HSCs in bone marrow or elsewhere. The blood output can be either increased or decreased. The increase or decrease of the blood output can, in some embodiments, be determined by measuring production of blood cells in the subject. In some embodiments, the measuring production of blood cells comprises determining the number of peripheral blood cells. Non-limiting examples of blood cell include red blood cells (also known as erythrocytes), white blood cells (also known as leukocytes), and platelets (also known as thrombocytes).

In some embodiments, the number, function, and/or activity of cells of hematopoietic origin, such as blood cells, in a subject can be regulated by administering a miRNA or an anti-miRNA oligonucleotide to HSCs or hematopoietic multipotent progenitor cells in bone marrow or elsewhere. In some embodiments, the miRNA is miR-125b1, miR-125b2, miR-126, miR-155, or a mixture thereof. In some embodiments, the miRNA is miR-196b, miR-181c, let7e, miR-542, or a mixture thereof. In some embodiments, the miRNA is miR-125b1 or miR-125b2. In some embodiments, the miRNA is miR-126. In some embodiments, the miRNA is miR-155. In some embodiments, the anti-miRNA is anti-miR-125b1, anti-miR-125b2, anti-miR-126, or anti-miR-155. In some embodiments, the anti-miRNA miRNA is anti-miR-125b1 or anti-miR-125b2.

In some embodiments, the blood output can be increased by administering miR-125b1, miR-125b2, miR-126, miR-155, or a mixture thereof to HSCs or hematopoietic multipotent progenitor cells in bone marrow or elsewhere. In some embodiments, the blood output can be decreased by administering anti-miR-125b1, anti-miR-125b2, anti-miR-126, anti-miR-155, or a mixture thereof to HSCs or hematopoietic multipotent progenitor cells in bone marrow or elsewhere. In some embodiments, the blood output can be decreased by administering miR-196b, miR-181c, let7e, miR-542, or a mixture thereof to HSCs or hematopoietic multipotent progenitor cells in bone marrow or elsewhere. In some embodiments, the blood output can be increased by administering anti-miR-196b, anti-miR-181c, anti-let7e, anti-miR-542, or a mixture thereof to HSCs or hematopoietic multipotent progenitor cells in bone marrow or elsewhere. Skill artisans will appreciate that, in some circumstances, the increase or decrease of blood output caused by the administration of miRNA or anti-miRNA oligonucleotide to HSCs or hematopoietic multipotent progenitor cells can be dose-dependent. The effective amount of miRNA oligonucleotide for increasing or decreasing blood output can be determined by skilled artisan using knowledge and techniques known in the art without undue experimentation.

In some embodiments, miR-125b, miR-126, and/or miR-155 can be used to treat subjects with low blood counts, for example, low red blood cell count, low white blood cell count, low platelet count, and any combination thereof. As disclosed above, production of blood cells in a subject can be increased by administering miR-125b, miR-126 and/or miR-155 oligonucleotides to HSCs in bone marrow or elsewhere, thereby increase the number of blood cells in the subject. Examples of diseases or disorders of low blood counts include, but are not limited to myelosuppression, pancytopenia, anemia (e.g., aplastic anemia and hemolytic anemia), thrombocytopenia, leucopenia, neutropenia, and granulocytopenia.

In some embodiments, the blood output in a subject can be increased by administering a miRNA or an anti-miRNA oligonucleotide to HSCs or hematopoietic multipotent progenitor cells in bone marrow or elsewhere. In some embodiments, the miRNA is miR-125b1, miR-125b2, miR-126, miR-155, or a mixture thereof.

In some embodiments, the blood output in a subject can be reduced or inhibited by administering a miRNA or an anti-miRNA oligonucleotide to HSCs or hematopoietic multipotent progenitor cells in bone marrow or elsewhere. In some embodiments, the miRNA is miR-196b, miR-181c, let7e, miR-542, or a mixture thereof.

In some embodiments, the number of myeloid cells, such as blood cells, in a subject can be regulated by administering a miRNA or an anti-miRNA oligonucleotide to HSCs or hematopoietic multipotent progenitor cells in bone marrow or elsewhere. In some embodiments, the miRNA is miR-125b1, miR-125b2, miR-126, or miR-155. In some embodiments, the miRNA is miR-125b1 or miR-125b2. In some embodiments, the anti-miRNA is anti-miR-125b1, anti-miR-125b2, anti-miR-126, or anti-miR-155. In some embodiments, the anti-miRNA is anti-miR-125b1 or anti-miR-125b2. In some embodiments, the number of myeloid cells in the subject is increased by administering a miRNA-125b oligonucleotide. Skill artisans will appreciate that, in some circumstances, the expansion or reduction in the number of myeloid cells caused by the administration of miRNA or anti-miRNA oligonucleotide to HSCs or hematopoietic multipotent progenitor cells can be dose-dependent. The effective amount of miRNA oligonucleotide for increase the number of myeloid cells can be determined by skilled artisans using knowledge and techniques known in the art without undue experimentation.

In some embodiments, hematopoietic stem cell engraftment in a subject, such as a mammal, can be promoted by administering a miRNA oligonucleotide to HSCs in bone marrow or elsewhere. The promotion of HSC engraftment can, in some embodiments, be determined by measuring proliferation of B cells, T cells, and/or myeloid cells in the subject. In some embodiments, the subject suffers from low blood count, a bone marrow failure disorder, and/or a hematopoietic malignancy. Non-limiting examples of bone marrow failure disorder include an inherited bone marrow failure syndrome such as Fanconi anemia, dyskeratosis congenital, and Diamond-Blackfan anemia; and acquired bone marrow failure such as aplastic anemia, myelodysplastic syndromes, paroxysmal nocturnal hemoglobinuria, and large granular lymphocyte leukemia.

The miRNA or antisense miRNA (e.g., miRNA-125b or antisense miRNA-125b) can be delivered as described herein or as known in the art. In some embodiments, delivery can be achieved by modification of an oligonucleotide encoding the miRNA or antisense miRNA. For example, a miR-125b, such as a mature miR-125b1 or miR-125b2, can be attached with cholesterol to facilitate penetration of the miR-125b into the cell membrane. Delivery can be optimized by using modified nucleotides or utilizing backbone modifications. Delivery can be achieved by injection into particular areas such as hematopoietic tissue or the bone marrow.

As disclosed herein, miR-125b is sufficient to cause leukemia, for example myeloid leukemia. Some embodiments provide methods for treating a myeloproliferative disorder in a mammal, where the method comprises administering an anti-miRNA (e.g., an antisense miRNA oligonucleotide) to target cells in the mammal, thereby inhibiting proliferation of myeloid cells. In some embodiments, the anti-miRNA is antisense miR-125b, miR-126, or miR-155 oligonucleotide. In some embodiments, the anti-miRNA is antisense miR-125b oligonucleotide. In some embodiments, the myeloproliferative disorder is polycythemia vera, essential thrombocytosis, myelosclerosis, or myeloid leukemia (e.g., acute myeloid leukemia and chronic myeloid leukemia). In some embodiments, the target cells are HSCs or hematopoietic multipotent progenitor cells.

EXAMPLES

Additional embodiments are disclosed in further detail in the following examples, which are not in any way intended to limit the scope of the claims.
Experimental Materials and Methods
The following experimental material and methods were used for Examples 1-4 described below.
Isolation of Bone Marrow Cell Subsets and FACS Hematopoietic stem and progenitor cells (HSPCs) were isolated from C57BL6 bone marrow by first depleting lineage-positive cells using specific biotinylated antibodies (shown in Table 1), magnetic beads, and a MACS column (Miltenyi). Viable (7-amino-actinomycin D[7-AAD] negative) neage-negative (lin−) cells were next stained with fluorophore-conjugated antibodies (Table 1) and separated using a FACS Aria (BD) into cKit−, cKit+Sca1−, and lin−cKit+Sca1+ (LKS) subpopulations. Hematopoietic stem cells were further purified from among the LKS population by sorting out endothelial protein C receptor (EPCR)+ or CD150+ CD48− LKS cells. CD11b+ and B220+ cells were fractionated from total bone marrow (BM) using a MACS column. RBC-depleted PBMCs were stained with the indicated antibodies (Table 1), washed, and analyzed using a FACSCalibur (BD).

TABLE 1

Antibodies used for experiments

| Target Antigen | Antibody Clone |
|---|---|
| mGr1 (Ly-6G) | RB6-8C5 |
| mCD11b | M1/70 |
| mTer-119 | TER-119 |
| mB220 (CD45R) | RA3-6B2 |
| mCD45.1 | A20 |
| mCD45.2 | 104 |
| mcKit | 2B8 |

TABLE 1-continued

Antibodies used for experiments

| Target Antigen | Antibody Clone |
|---|---|
| mSca1 (Ly6A/E) | D7 |
| mCD150 | TC15-12F12.2 |
| mCD48 | HM48-1 |
| mEPCR (CD201) | eBio1560 |
| mCD4 (L3T4) | GK1.5 |
| mCD8a (Ly-2) | 53-6.7 |
| mCD11c (p150/90) | N418 |
| mNK-1.1 (Ly-55) | PK136 |
| mCD3e | 145-2C11 |
| mCD19 | MB19-1 |
| hCD45 | H130 |
| hCD19 | HIB19 |
| hCD33 | HIM3-4 |
| hCD34 | 4H11 |

Microarray Analysis

For the microarray, total RNA was collected from equal numbers of LKS cells and total RBC-depleted BM using the miRNeasy kit (Qiagen) and subsequently used for a lowinput microarray with Agilent mouse microRNA (miRNA) 10.1 chips (Asuragen). Data represent miRNA-expression levels in LKS and total bone marrow taken from 10 mice and pooled before RNA purification. Two biological replicates were analyzed, and both identified the following 11 miRNAs as miRNAs enriched in LKS cells: miR125a-5p, miR-125b-5p, miR-155, miR-130a, miR196b, miR-99a, miR-126-3p, miR-181c, miR-193b, miR-542-5p, and let7e.
Quantitative PCR ABI Taqman was used to quantitate microRNA levels in different BM cell populations using gene-specific primers according to the manufacturer's instructions.
Competitive Bone-Marrow Reconstitutions C57BL6 mice expressing the congenic WBC markers CD45.1 or CD45.2 were used as bone-marrow donors, and CD45.2 mice were used as recipients. Equal numbers of HSPC-enriched bone-marrow cells from each group (obtained from mice treated with 5-fluorouracil for 5 days) were infected with a miRNA-expressing (CD45.1 cells) or control vector (CD45.2 cells), and a 1:1 cell mixture was injected i.v. into lethally irradiated mice.
Retroviral and Lentiviral Vectors miRNA-expression constructs formatted with miR-155 loop and arms were constructed as described in O'Connell et al. Proc. Natl. Acad. Sci. USA 106:7113-7118 (2009), which is incorporated by reference herein. Sequences of the oligonucleotides and PCR primers used are shown in Table 2.

TABLE 2

Oligonucleotide and PCR Primer Sequences

| Primer | Sequence |
|---|---|
| miR-125a 155-formatted template | GAAGGCTGTATGCTGTCCCTGAGACCCTTTAACCTGTG AGTTTTGGCCACTGACTGACTCACAGGTAAGGGTCTCA GGGACAGGACACAAGGCCTG (SEQ ID NO: 60) |
| miR-125b 155-formatted template | GAAGGCTGTATGCTGTCCCTGAGACCCTAACTTGTGAG TTTTGGCCACTGACTGACTCACAAGTGGGTCTCAGGGA CAGGACACAAGGCCTG (SEQ ID NO: 61) |
| miR-155 155-formatted template | GAAGGCTGTATGCTGTTAATGCTAATTGTGATAGGGGT TTTGGCCACTGACTGACCCCTATCAATTAGCATTAACA GGACACAAGGCCTG (SEQ ID NO: 62) |
| miR-99a 155-formatted template | GAAGGCTGTATGCTGAACCCGTAGATCCGATCTTGTGG TTTTGGCCACTGACTGACCACAAGATGATCTACGGGTT CAGGACACAAGGCCTG (SEQ ID NO: 63) |

TABLE 2-continued

Oligonucleotide and PCR Primer Sequences

| Primer | Sequence |
|---|---|
| miR-126 155-formatted template | gaaggctgtatgctgCATTATTACTTTTGGTACGCGGTTTTGGC CACTGACTGACCGCGTACCAAGTAATAATGcaggacacaagg cctg (SEQ ID NO: 64) |
| miR-196b 155-formatted template | GAAGGCTGTATGCTGTAGGTAGTTTCCTGTTGTTGGGG TTTTGGCCACTGACTGACCCCAACAAGGAAACTACCTA CAGGACACAAGGCCTG (SEQ ID NO: 65) |
| miR-130a 155-formatted template | GAAGGCTGTATGCTGCAGTGCAATGTTAAAAGGGCATG TTTTGGCCACTGACTGACATGCCCTTAACATTGCACTG CAGGACACAAGGCCTG (SEQ ID NO: 66) |
| miR-542-5p 155-formatted template | gaaggctgtatgctgCTCGGGGATCATCATGTCACGAgttttggccact gactgacTCGTGACAATGATCCCCGAGcaggacacaaggcctg (SEQ ID NO: 67) |
| miR-181c 155-formatted template | gaaggctgtatgctgAACATTCAACCTGTCGGTGAGTgttttggccact gactgacACTCACCGAGGTTGAATGTTcaggacacaaggcctg (SEQ ID NO: 68) |
| miR-193b 155-formatted template | GAAGGCTGTATGCTGAACTGGCCCACAAAGTCCCGCTG TTTTGGCCACTGACTGACAGCGGGACTGTGGGCCAGTT CAGGACACAAGGCCTG (SEQ ID NO: 69) |
| let7e 155-formatted template | GAAGGCTGTATGCTGTGAGGTAGGAGGTTGTATAGTTG TTTTGGCCACTGACTGACAACTATACCCTCCTACCTCAC AGGACACAAGGCCTG (SEQ ID NO: 70) |
| miR-125b-1 NotI Fw | TTCGCGGCCGCGAGTTTTCTCTGATGTACTCGTGATCGTATGT (SEQ ID NO: 71) |
| miR-125b-1 XhoI Rev | TTCCTCGAGAACAGAAATCCAGGAGCTGCCACTC (SEQ ID NO: 72) |
| miR-125b-2 NotI Fw | TTCGCGGCCGCGCCCTTGCTAGCGAAGCAGATTTT (SEQ ID NO: 73) |
| miR125b-2 XhoI Rev | TTCCTCGAGAGTATTTTTGGGGATGGGTCATGGTG (SEQ ID NO: 74) |

Endogenous miR-125b-1 and miR-125b-2 sequences were PCR cloned into MG and MGP retrovectors as described in O'Connell et al. Proc. Natl. Acad. Sci. USA (2009) and O'Connell et al. J Exp Med 205:585-594 (2008) or a third-generation replication-deficient lentiviral vector with an elongation factor 1α (EF1α) promoter. Retroviral transduction of mouse HSPCs and bone-marrow transplantation were performed as previously in O'Connell et al. Proc. Natl. Acad. Sci. USA (2009) and O'Connell et al. J Exp Med 205:585-594 (2008). K562 cells were cultured in complete RPMI medium and infected with retrovectors in the presence of polybrene (10 μg/mL). Lentiviral transduction of CD34+ cells was achieved using an multiplicity of infection (MOI) of 4 or 40, Retronectin-coated plates (Fisher Scientific), and StemSpan serum-free medium (Stem Cell Technologies). Transduced CD34+ cells were washed and injected 24 hours after infection.

Human Immune System Mouse Model

Human immune system (HIS) mice were generated by injecting 2×10⁵ lentivirus transduced CD34+ CB cells intra-hepatically into irradiated newborn Rag2-/-γc-/- mice on a BALB/c genetic background as described in Traggiai et al. Science 304:104-107 (2004). Human hematopoietic cell engraftment was assessed by collecting blood and subjecting peripheral blood mononuclear cells (PBMCs) to FACS.

Histopathology and Complete Blood Cell Counts

These procedures were performed as described in O'Connell et al. Proc. Natl. Acad. Sci. USA (2009) and O'Connell et al. J Exp Med 205:585-594 (2008).

Statistics

For statistical analysis, a Student two-tailed t test was used.

Example 1

Identification of miRNAs Enriched in HSCs

Lineage-negative (lin−) cKit+Sca1+ (LKS) cells were isolated from 10 adult C57BL6 mouse BM using FACS (FIG. 1A Upper). Total RNA was isolated from LKS cells as well as RBC-depleted total bone marrow (BM). The total RNA was used to perform a microarray analysis to identify expression of mouse miRNAs. 137 miRNAs were expressed at detectable levels in the BM and/or LKS population. Among those 137 miRNAs, 67 were expressed at higher levels in total BM vs. LKS cells, 59 were expressed at similar levels in the two cellular populations, and 11 were expressed at higher levels in the LKS compartment vs. total BM. See FIG. 1A Lower Corroborating the microarray results, quantitative PCR (qPCR) also detected enrichment of those 11 miRNAs in LKS cells. As shown in FIG. 1B, those 11 miRNAs are miR125a-5p, miR-125b-5p, miR-155, miR-130a, miR196b, miR-99a, miR-126-3p, miR-181c, miR-193b, miR-542-5p, and let7e.

Figure 2:
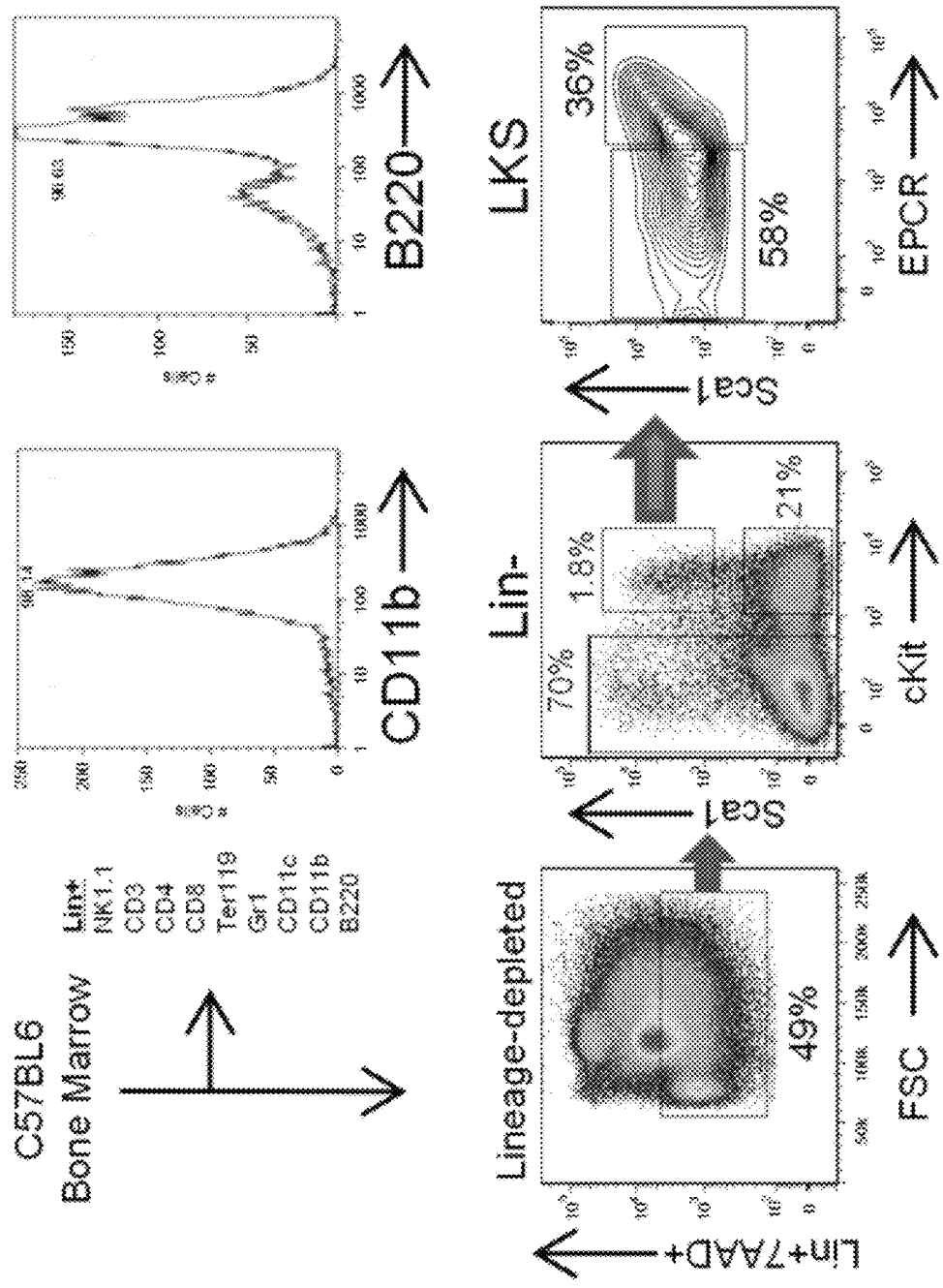
FIG. 2 shows an extensive cellular fractionation scheme that was used to further assess the expression profiles of 11 miRNAs enriched in LKS cells.

A more extensive cellular fractionation of mouse BM further confirmed enrichment of most of these miRNAs in the LKS subset (FIG. 1C and FIG. 2). Expression of miR-223, known to be enriched in mature myeloid cells, was measured as a control (FIG. 1C). The LKS population is comprised of both HSCs, capable of establishing long-term multilineage hematopoietic engraftment, and multipotent progenitors, with reduced capacity to reconstitute the hematopoietic system. LKS cells expressing the HSC marker endothelial protein C receptor (EPCR) were first analyzed, and a higher relative expression of many of the miRNAs under study was found in EPCR+ vs. EPCR-LKS cells (FIG. 1C). Long-term HSCs have also been shown to be CD150+CD48−, whereas other LKS progenitor populations are negative for CD150. Again, qPCR analysis found that most of the 11 miRNAs enriched in LKS cells were further enriched in CD150+ CD48− long-term HSCs compared with CD150−LKS cells (FIG. 1D). These data indicate, using multiple criteria to define HSCs, that this subset of miRNAs is largely enriched in long-term HSCs.

Example 2

Impact of HSC miRNAs on Long-Term Hematopoietic Engraftment

This example discloses the functional impact of the 11 HSC-enriched miRNAs disclosed in Example 1 on long-term hematopoietic reconstitution.

Figure 3:
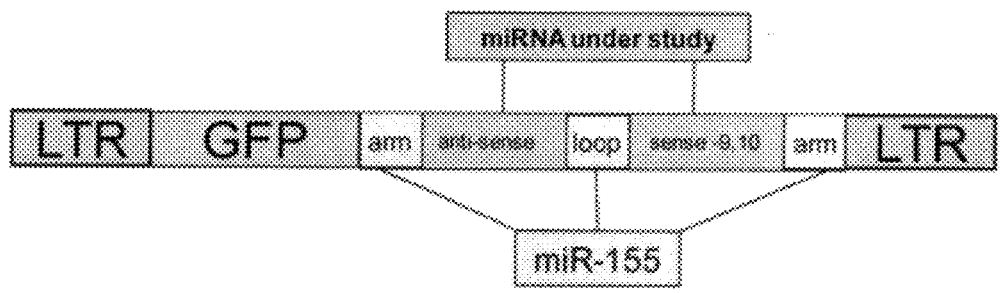
FIG. 3 shows the impact of HSC-enriched miRNAs on long-term hematopoietic reconstitution. (A) Schematic representation of the MSCV-based retroviral vector (MG) used to express HSC-enriched miRNAs using a miR-155 arms and loop format. (B) Competitive BM reconstitution showing engraftment potential of BM expressing each of the 11 HSC-enriched miRNAs (CD45.1 cells) compared with the control. (C) Lineage analysis of the CD45.1+GFP+ peripheral blood cells at the 4-month time point: B220+ (B cell), CD3+ (T cell), and CD11b+(myeloid cell). Data represent the mean+ SEM.
Figure 3:
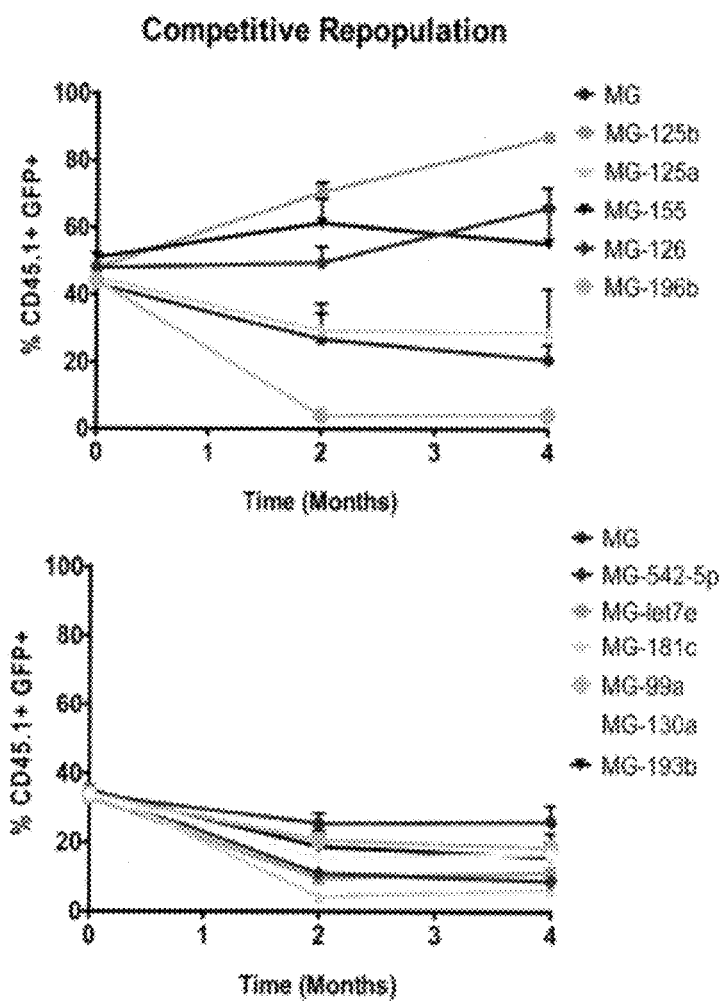
Figure 3:
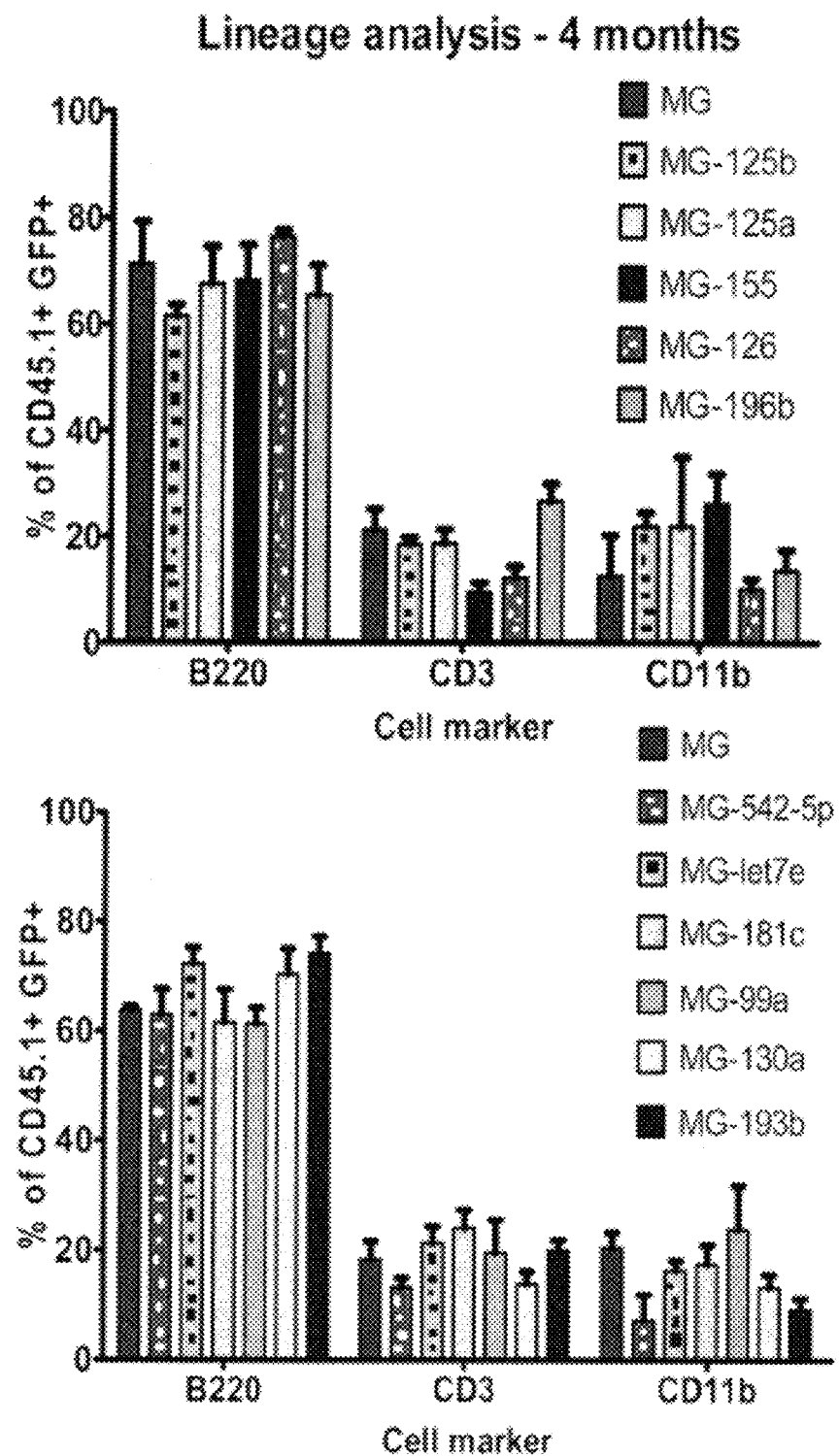
Figure 4:
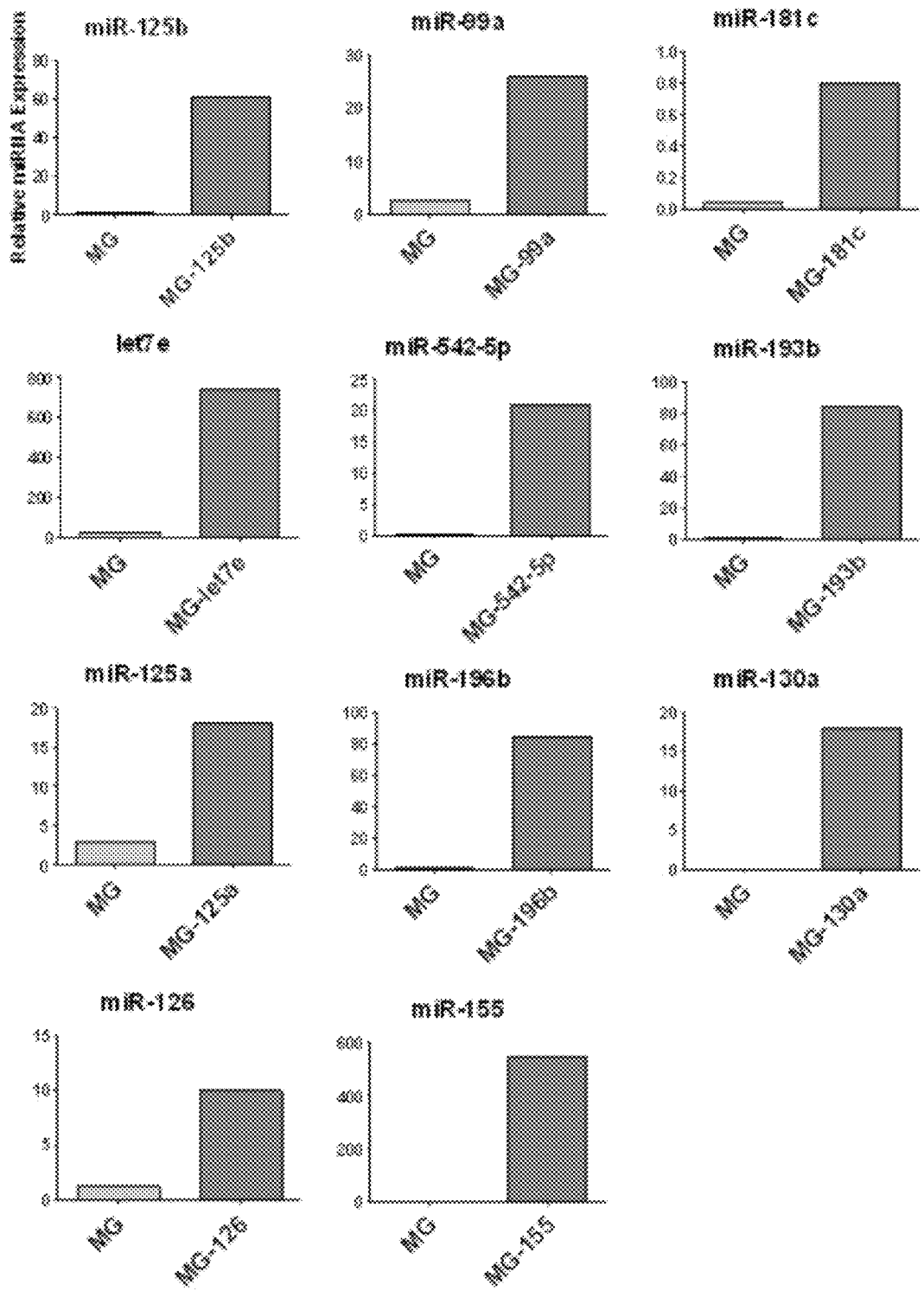
FIG. 4 shows expression levels of 11 miRNAs enriched in LKS cells using corresponding miRNA-expressing MG vectors. miRNA levels were assessed by Quantitative PCR (qPCR) and normalized to RNU48.

A series of murine stem-cell virus (MSCV)-based miRNA-expression constructs that carry each of the HSC-enriched 11 miRNAs were constructed. The vectors were formatted with mouse miR-155 arms and stem loop sequences, with each miRNA duplex encoded by the sense and antisense stem regions (FIG. 3A). This format was chosen because of its established ability to be processed in hematopoietic cells, including HSCs, where mature miR-155 has been found be expressed (FIG. 1). Production of the different mature miRNAs using this format was confirmed in 293T cells by qPCR (FIG. 4).

Competitive BM reconstitutions were performed using C57BL6 mice to assess the engraftment potential of BM expressing each of the 11 HSC-enriched miRNAs (CD45.1 cells) compared with control BM (CD45.2 cells). GFP was used to identify cells containing a vector. A 4-month time course showing the percentage of CD45.1+GFP+ cells in the peripheral blood of each group of mice is shown in FIG. 3B. The experiment was broken into two batches (FIG. 3B Upper and Lower), each with its own negative control.

Figure 5:
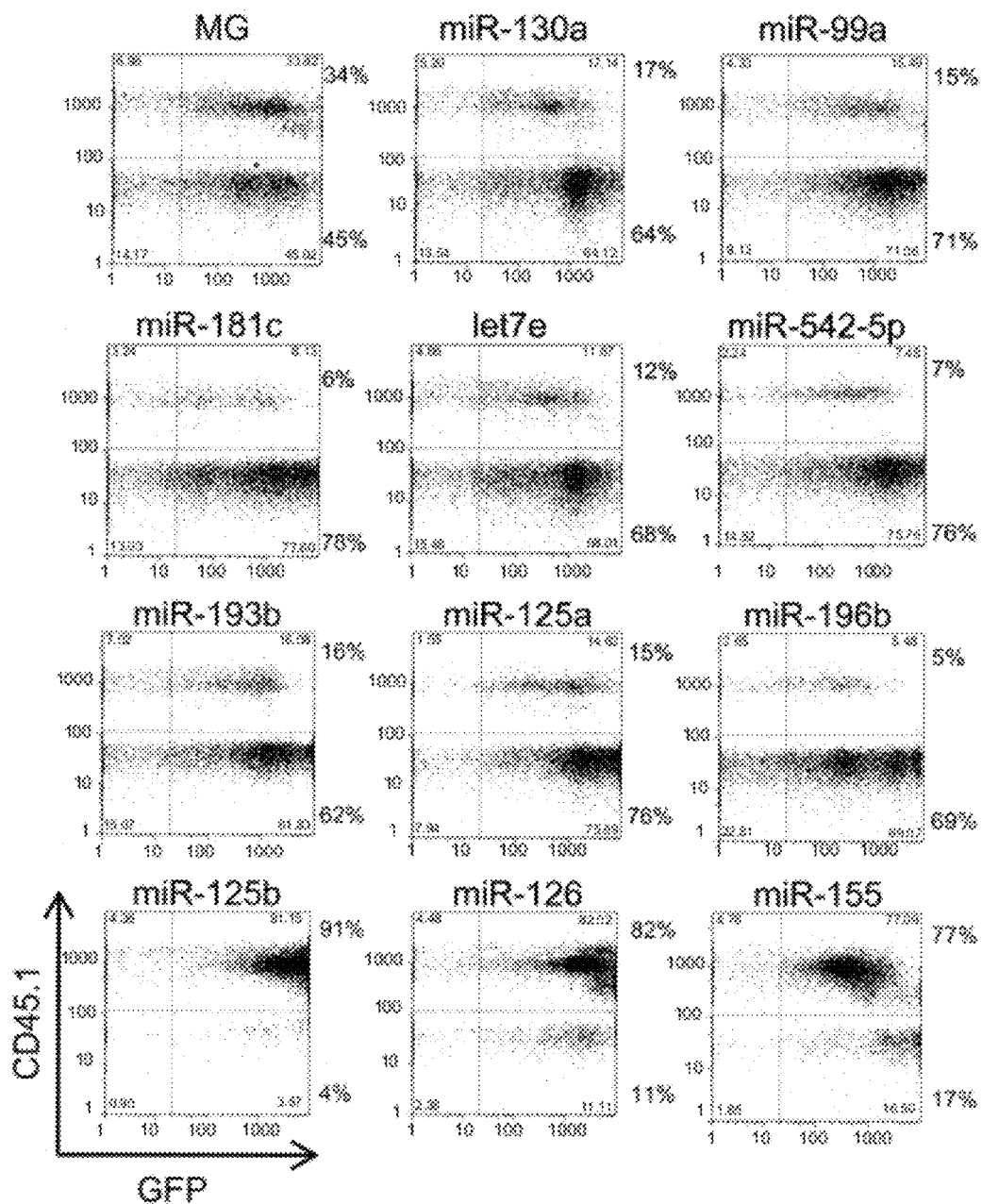
FIG. 5 shows FACS plots of PBMCs from mouse groups having BM expressing each of the 11 HSC-enriched miRNAs (n=4 at 4 month postreconstitution). GFP was used to identify cells containing the vectors.

Competitive repopulation experiments were performed by combining equal numbers of HSC-enriched CD45.1+ bone-marrow cells transduced with retroviruses encoding a specific HSC miRNA with HSC-enriched CD45.2+ bone marrow transduced with a control retrovirus. This cellular mixture was used to reconstitute lethally irradiated CD45.2+ C57BL6 recipients. Because the retrovectors coexpress GFP in addition to a miRNA, the ability of the CD45.1+ miRNA-expressing bone marrow to compete with CD45.2+ control vector-containing bone marrow during hematopoietic engraftment could be tracked by FACS analysis of peripheral blood cells. Mice were bled at 2 and 4 month postreconstitution. When both vectors lacked a miRNA, there was similar representation of the two markers in the peripheral blood mononuclear cells (FIG. 5). In three cases, including miR-125b-5p, miR-126-3p, and miR-155, the miRNA conferred an evident and statistically significant (P<0.05) competitive advantage to the engrafted bone marrow (FIGS. 3B and 5). Among the 3 miRNA, miR-125b had the largest positive impact on competitive reconstitution (FIGS. 3B and 5). In contrast, overexpression of several of the miRNAs caused a significant (P<0.05) disadvantage to the engrafted bone marrow, with miR-196b, miR-181c, let7e, and 542-5p having the largest impact (FIGS. 3B and 5).

FACS analysis of the peripheral blood was also used to determine the distribution of different hematopoietic lineages to assess whether engraftment was being skewed to a single lineage or was multilineage at 4 month postreconstitution. Lineage analysis of the CD45.1+GFP+ peripheral blood cells at the 4-month time point was assessed by determining the percentages of B220+ (B cell), CD3+ (T cell), and CD11b+ (myeloid cell) in each group. As shown in FIG. 3C, the effects of the different miRNAs on engraftment were largely multilineage, consistent with these miRNAs regulating stem-cell homeostasis.

Figure 6:
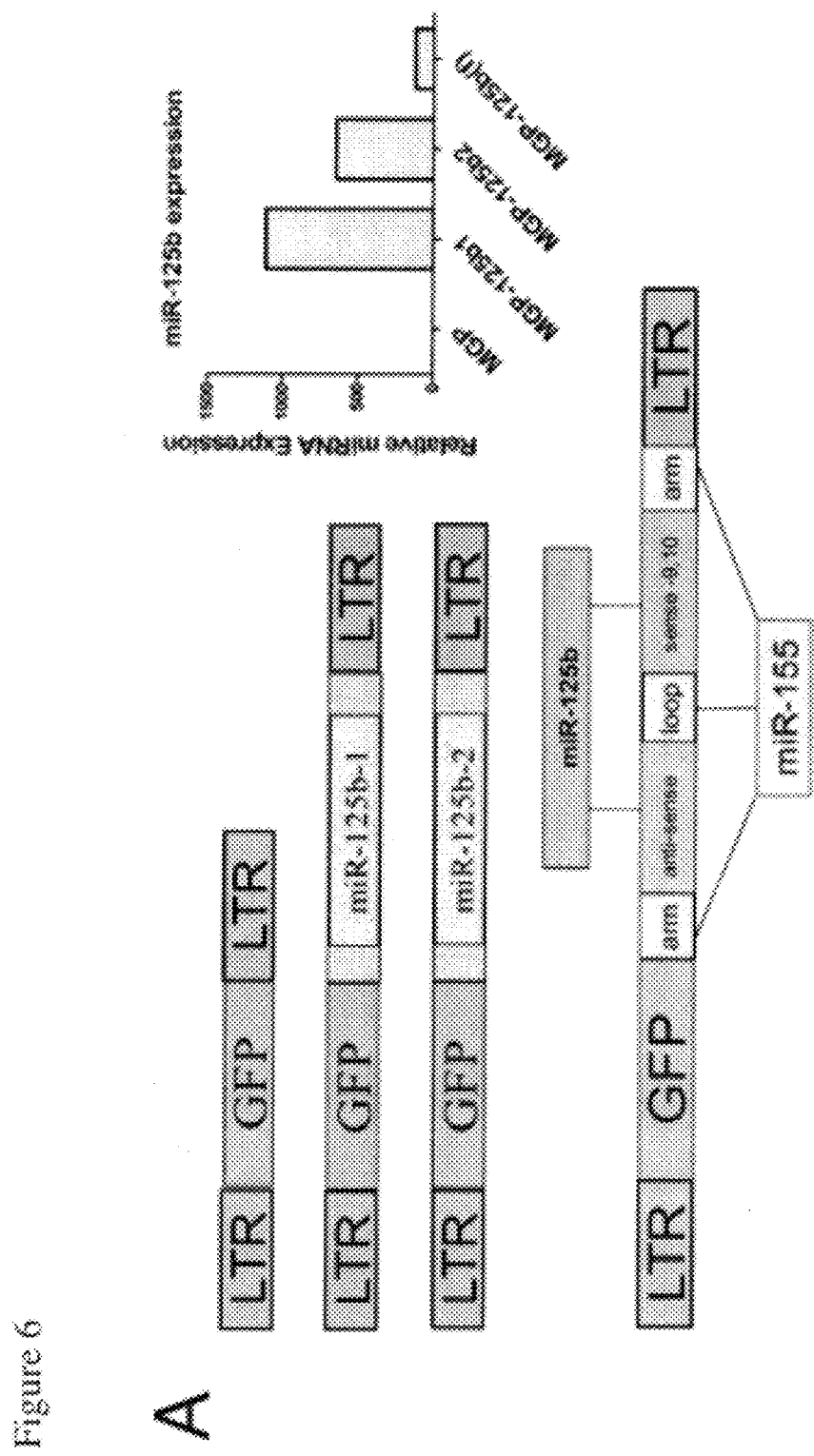
FIG. 6 shows that miR-125b causes a dose-dependent myeloproliferative disorder (MPD). (A) Schematic representation of the three expression constructs used to express miR-125b (left panel) and expression level of miR-125b from the three expression constructions (right panel). (B) Blood concentrations of the indicated cell types for mice expressing MG, MG-125b1, MG-125b2, and in a separate experiment (separated by a dashed line), MG and MG-125b(f) 2-month postreconstitution. (C) FACS plot showing Gr1+CD11b+ cells in the peripheral blood of mice overexpressing miR-125b2, miR-125b1, or control vector 2 month postreconstitution. Asterisk denotes a P value<0.05.
Figure 6:
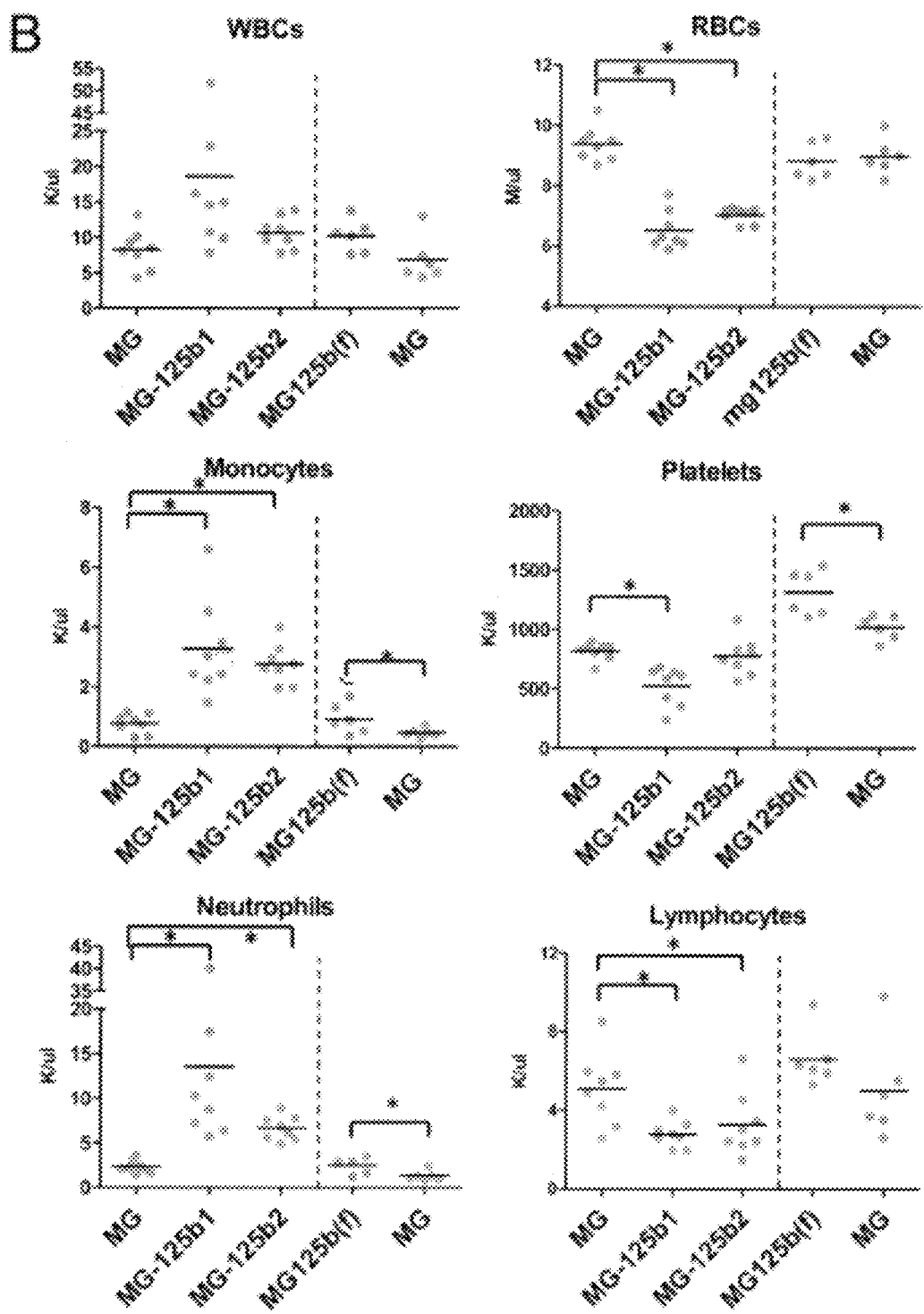
Figure 6:
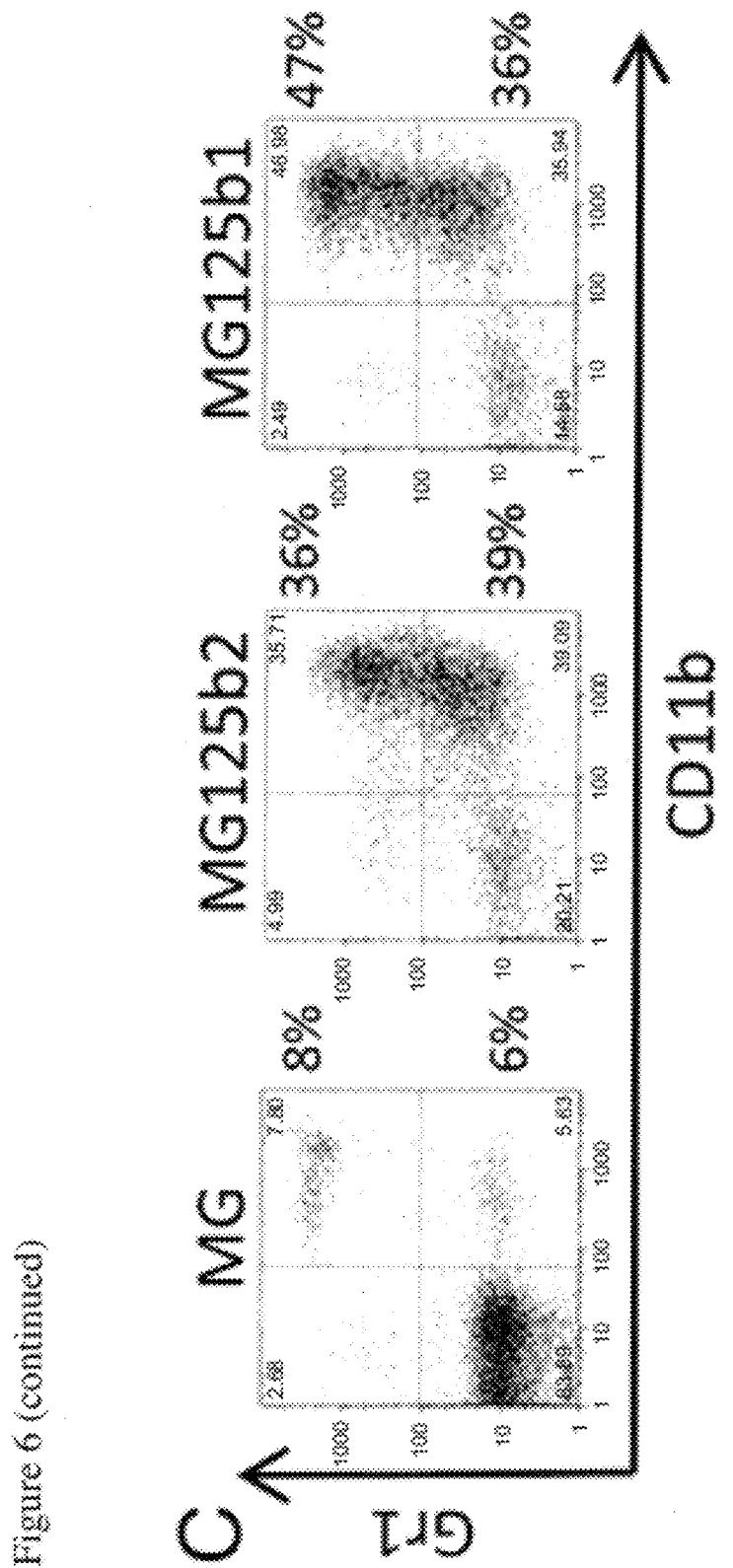

Example 3 miR-125b Causes a Dose-Dependent Myeloproliferative Disorder that Progresses to a Myeloid Leukemia To assess the impact of expressing miR-125b with its native arms and loop sequences, segments of the miR-125b1 and miR-125b2 primary transcripts were cloned into the retroviral expression system shown in FIG. 6A. K562 cells were transduced with each retrovector, and miR-125b levels were assayed by qPCR. The resulting cassettes were found to lead to substantially increased expression levels of mature miR-125b in K562 cells compared with the miR-125b cassette formatted with miR-155 arms and loop sequences [used in Example 2 and referred to as 125b(f) in this Example], likely a result of more efficient processing (FIG. 6A). As shown in FIG. 6A, miR-125b1 expression was higher than miR-125b2, and thus three vectors had conveniently graded expression of miR-125b.

Mice were subsequently reconstituted with bone marrow expressing miR-125b1, miR-125b2, or control vector, and a separate cohort of mice expressing miR-125b(f) or its vector control was also established. All mice from both groups were bled after 2 months of reconstitution, and complete blood cell counts (CBCs) were recorded (FIG. 6B). Mice expressing miR-125b, regardless of the construct used, had subtly elevated total WBC counts compared with control mice. Reconstitution of mice with HSPCs expressing the lowest levels of miR-125b (i.e., the mice having the miR-125b(f) expression vector), resulted in a general increase in all WBC compartments analyzed, including myeloid, lymphoid, and platelets, but did not impact RBCs. However, mice with the more highly expressed endogenous miR-125b1 or b2 vectors exhibited a clear myeloproliferative disorder (MPD) that was characterized by increased absolute numbers of monocytes and neutrophils and decreased levels of lymphocytes, RBCs, and platelets. Peripheral blood from miR-125b-1- and miR-125b-2-expressing mice, compared with control mice, also had dramatic increases in the percentage of CD11b+ myeloid cells, many of which were also Gr1+ as assayed by FACS (FIG. 6C).

Figure 7:
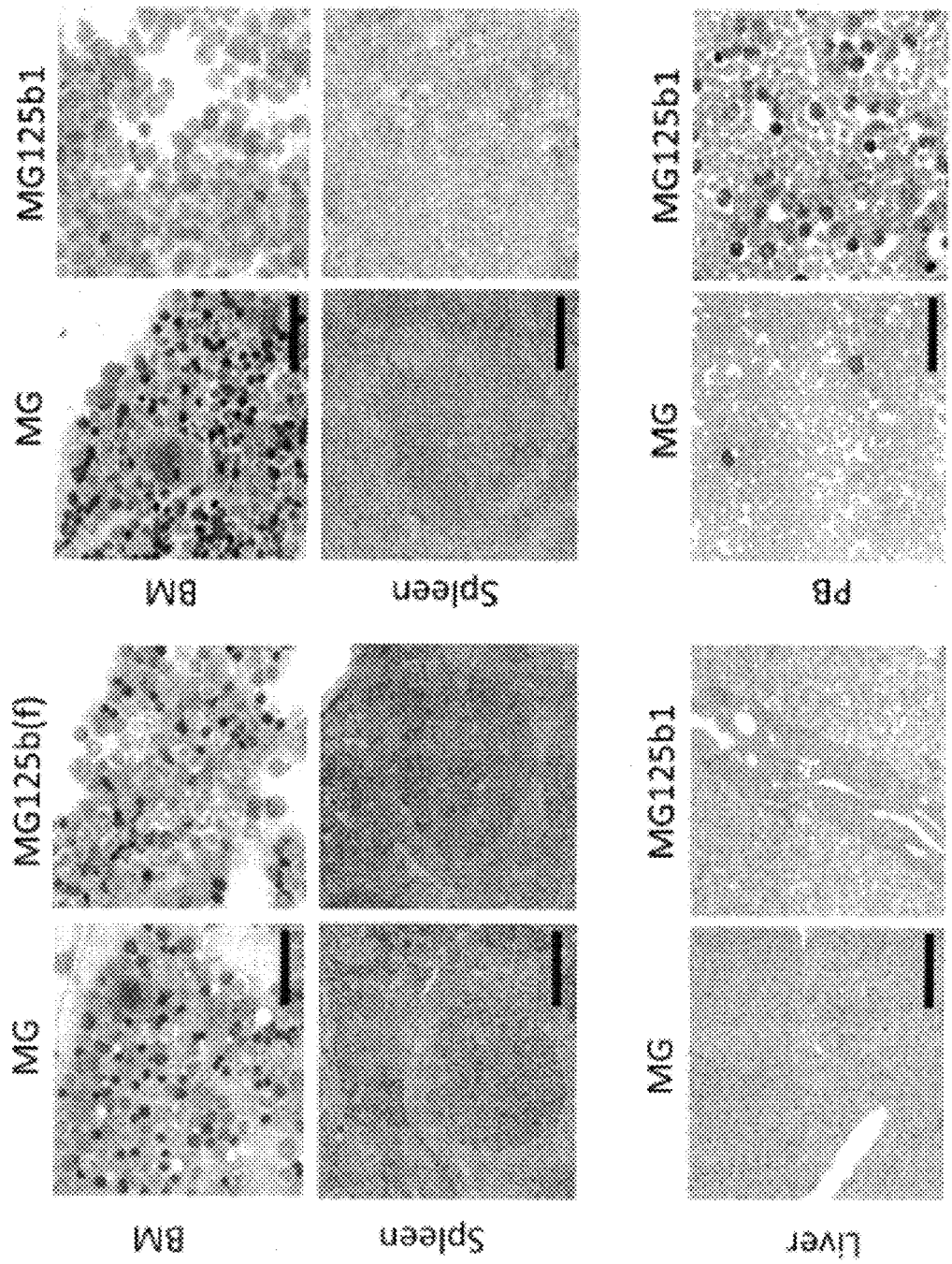
FIG. 7 shows pathological analysis of miR-125b-expressing mice. Wright-stained BM smears and H&E-stained spleen sections from MG and MG-125b(f)-expressing mice 2 months after reconstitution are shown in Upper Left, and the same tissues and liver from miR-125b1-expressing mice 2.5 months postreconstitution are shown in Upper Right and Lower Left. Wright-stained blood smears from MG- and MG-125b1-expressing mice 3.5 months after bone-marrow reconstitution are shown in Lower Right. Data represent at least two independent experiments. (Scale bar: spleen and liver, 200 mm; blood and bone marrow, 40 mm.)
Figure 8:
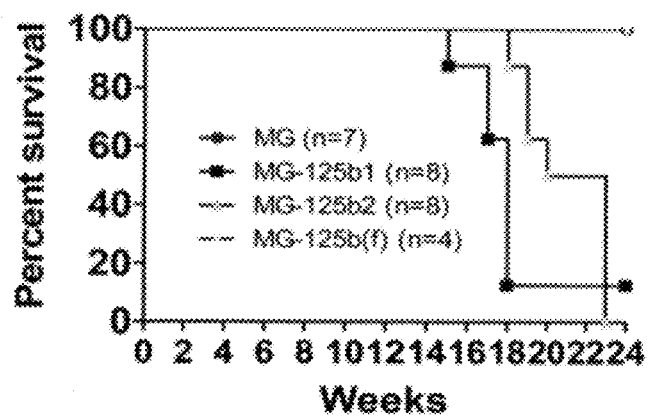
FIG. 8 shows that the MPDs caused by miR-125b progressed to myeloid leukemia in a dosedependent manner. (A) Percent survival in mice expressing different levels of miR-125b. (B) Liver and spleen from miR-125b2-expressing mice with leukemia 4.5 months postreconstitution. Representative H&E-stained tissue sections of each respective organ taken from miR-125b2-expressing mice are shown on Right. (C) Percentage of leukemic blasts in the peripheral blood of control or miR-125b2-expressing mice 3.5 and 4.5 month postreconstitution, and representative Wright-stained blood smears from miR-125b2 mice at each time point. Examples of blasts are indicated by arrows. (D) Percent survival of mice after i.v. transfer of malignant MG-125b1 (four different donors) or MG control bone marrow to Rag2−/−γc−/− recipients (n=3-6 mice per group). Asterisk denotes a P value<0.05.
Figure 8:
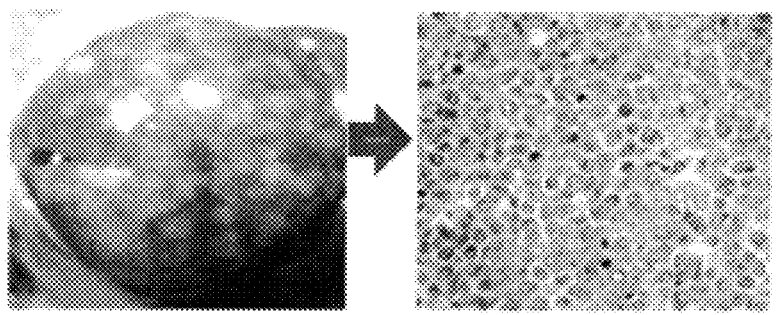
Figure 8:
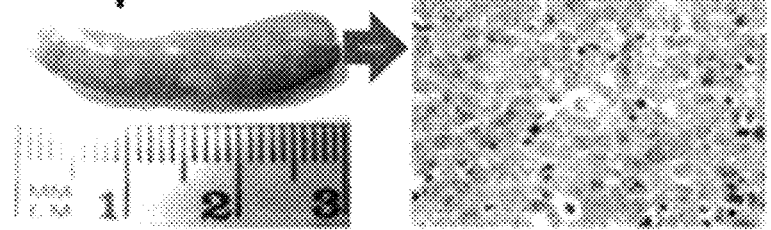
Figure 8:
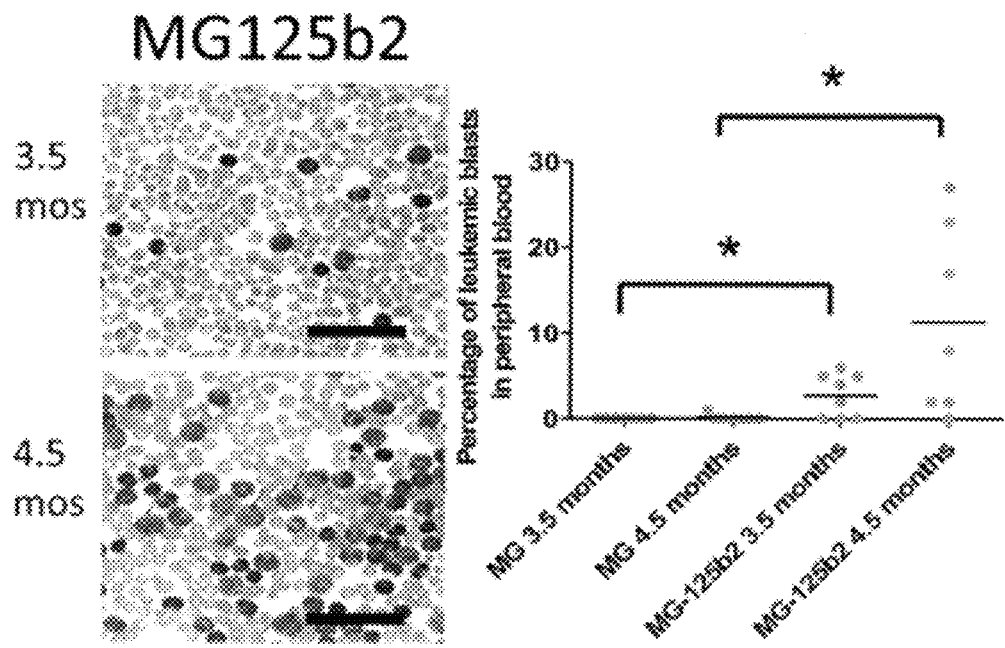
Figure 8:
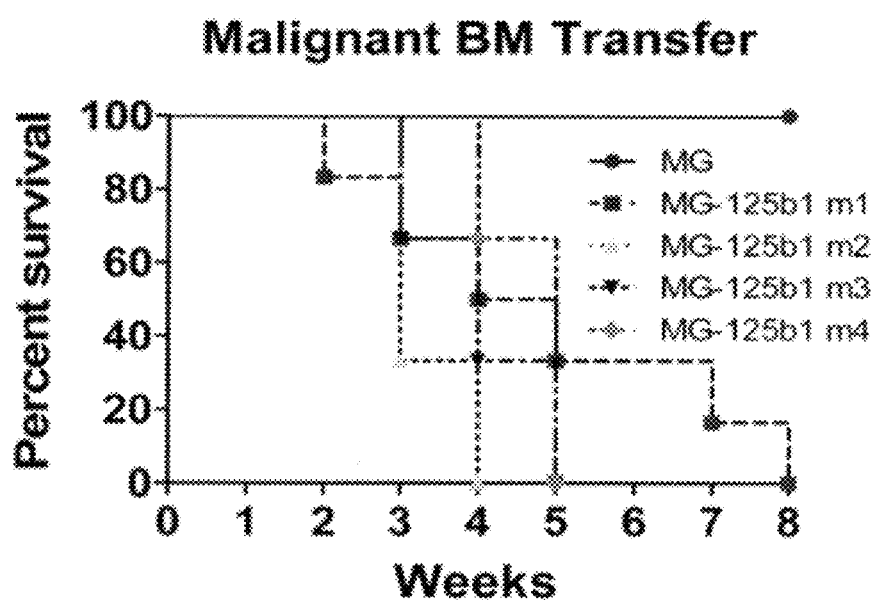

Analysis of Wright-stained bone-marrow smears from miR-125b(f) mice 2 months postreconstitution revealed a mild expansion of myeloid cells in the bone marrow, whereas H&E-stained spleen sections were similar to those from control mice (FIG. 7). However, miR-125b1- and miR-125b2-expressing mice exhibited myeloid-dominated BM and spleens as well as myeloid-cell infiltration into the liver (FIG. 7). By 3.5 months postreconstitution, miR-125b1 and miR-125b2 mice had substantially increased WBCs in their peripheral blood consisting mainly of immature granulocytic and monocytic cells (FIG. 7). Shortly after, the condition became lethal for most of the mice expressing the highest levels of miR-125b, with tumor infiltration evident in the spleen and liver (FIGS. 8A-B). The surviving miR-125b2 mice had progressively increasing WBC counts and higher levels of leukemic blasts in their peripheral blood from 3.5 to 4.5 months postreconstitution and also eventually succumbed to leukemia (FIGS. 8A and 8C). Furthermore, transfer of malignant BM from moribund miR-125b1-expressing mice to immunodeficient Rag2−/−γc−/− secondary recipients resulted in death within weeks, whereas transfer of BM from control mice had no impact on survival (FIG. 8D). These results show a dose-dependent sufficiency of miR-125b to drive pathological myeloid-cell expansion, a condition that progresses to an aggressive myeloid leukemia.

Example 4

Evolutionarily Conserved miRNA Expression and Function in Human CD34+ HSPCs

This example demonstrates that the 11 HSC-enriched miRNAs disclosed in Example 1 are also enriched in human CD34+ hematopoietic stem and progenitor cells (HSPCs).

Human umbilical cord blood (CB) was sorted into CD34+ (HSPC+) and CD34− (HSPC−) fractions. RNA was prepared from CD34+ and CD34−CB peripheral blood mononuclear cells (PBMC)s and expression of the miRNAs enriched in mouse HSCs were measured by qPCR. Data are normalized to RNU48 and presented as mean+SEM (n=3 different donors). With the exception of miR-193b, all of the 11 miRNAs showed significant enrichment in the CD34+ HSPC cellular subset compared with mature CD34−PBMCs (FIG. 9A).

Figure 9:
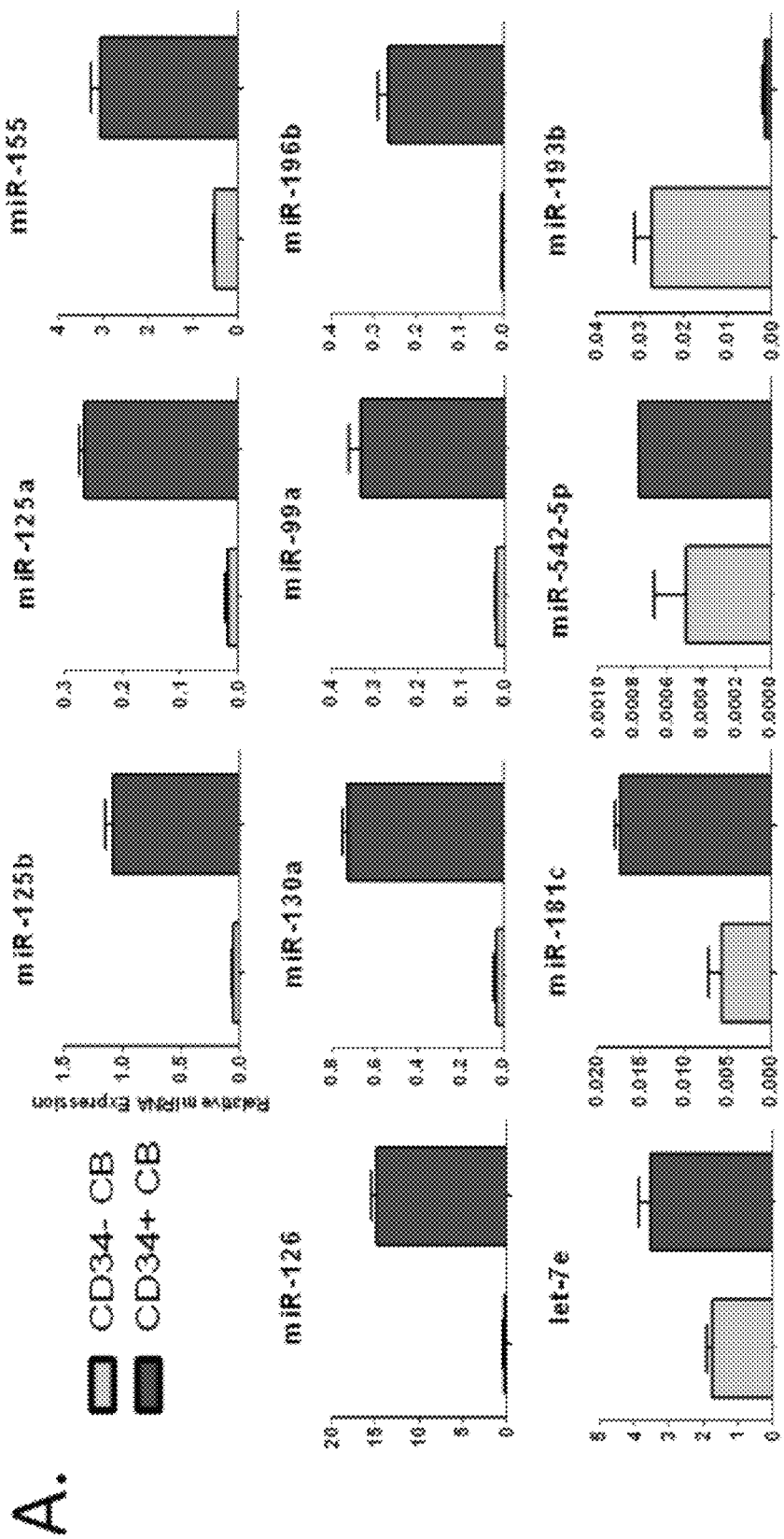
FIG. 9 shows evolutionarily conserved miRNA expression and function in human CD34+ HSPCs. (A) Expression of miRNAs that are enriched in mouse HSCs in human umbilical cord blood (CB) cells. Data are normalized to RNU48 and presented as mean+SEM (n=3 different donors). (B) Relative miRNA expression in human CB CD34+ cells transduced with control or miR-125b1-expressing lentiviral vectors at an MOI of about 4 or 40. (C) FACS plots showing an increased ratio of human to mouse CD45+ WBCs in the peripheral blood of miR-125b-expressing HIS mice 10 weeks after CD34+ cell injection. (D) Scatter plots showing percentage of human CD45+ WBCs in the peripheral blood of miR-125b-expressing HIS mice 10 weeks after CD34+ cell injection. Each gray dot represents a mouse. (E) Histograms showing percentages of human CD19 cells (B cells) and CD33 cells (myeloid cells) in the peripheral blood of high-dose (MOI 40) HIS mice. Data are represented as the mean±SEM. (F) A FACS plot showing human CD45+ and CD34+ cells in the BM of miR-125b-expressing and control vector HIS mice 12 weeks post-CD34+ injection. (G) Scatter plots showing percentage of human CD45+ and CD34+ cells in the BM of miR-125b-expressing and control vector HIS mice 12 weeks post-CD34+ injection. Each gray dot represents a mouse. Asterisk denotes a P value<0.05.
Figure 9:
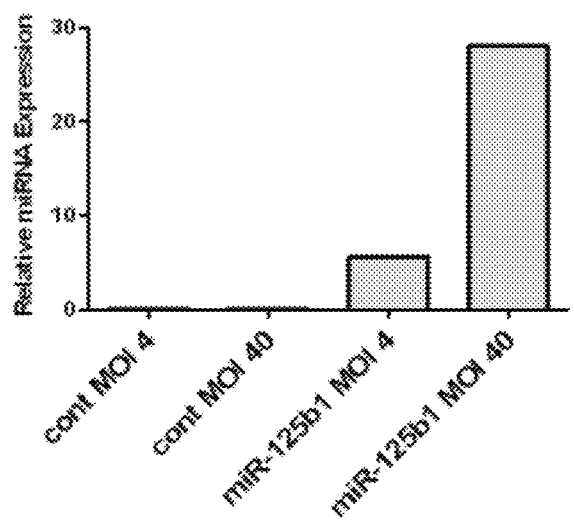
Figure 9:
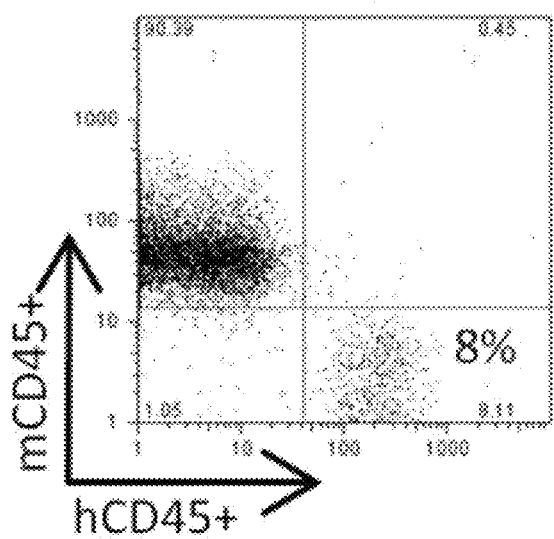
Figure 9:
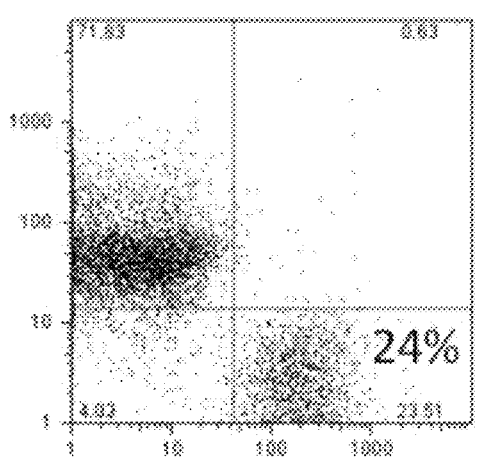
Figure 9:
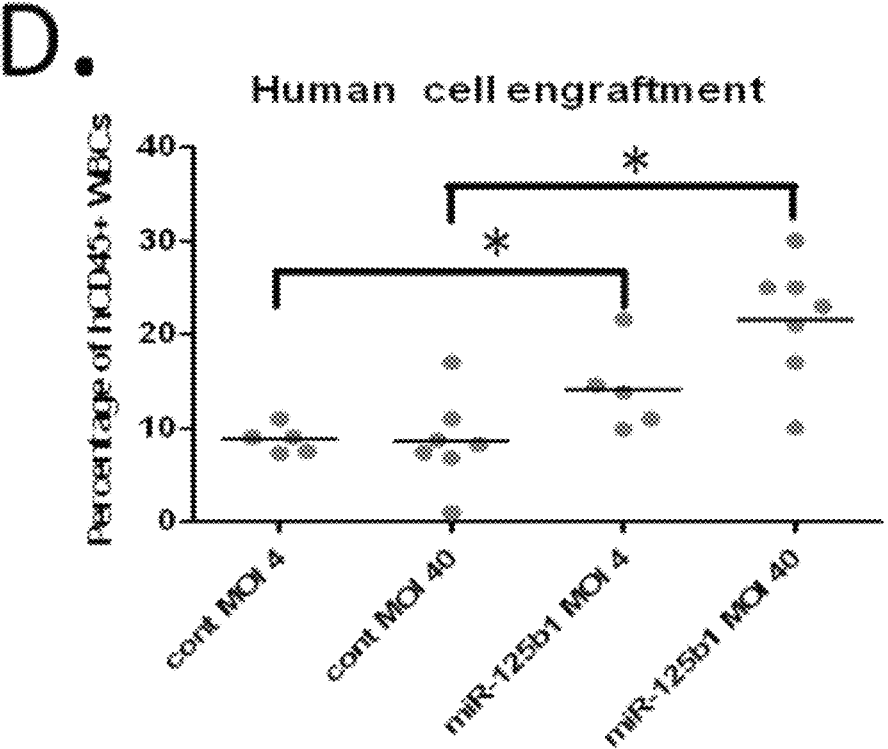
Figure 9:
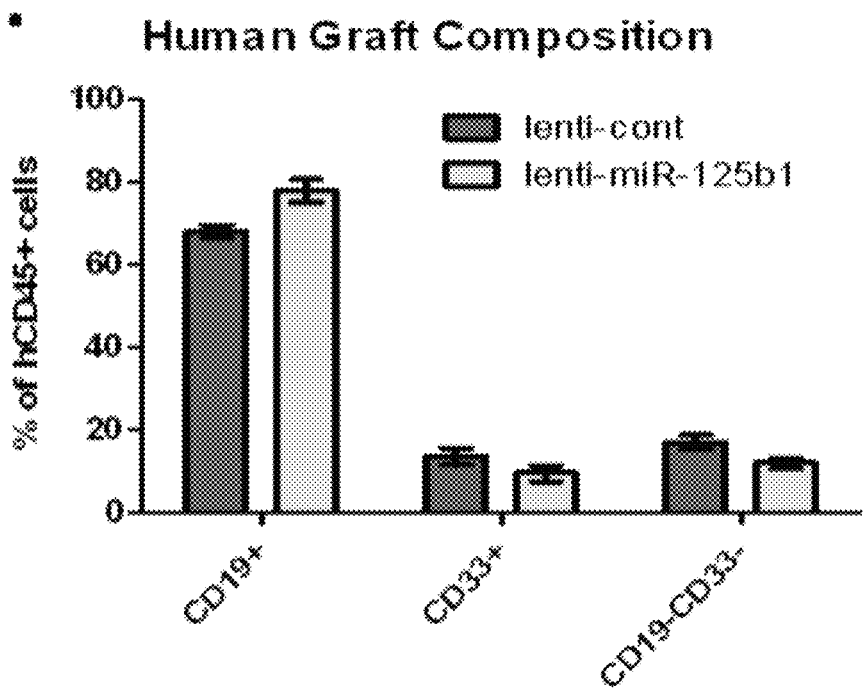
Figure 9:
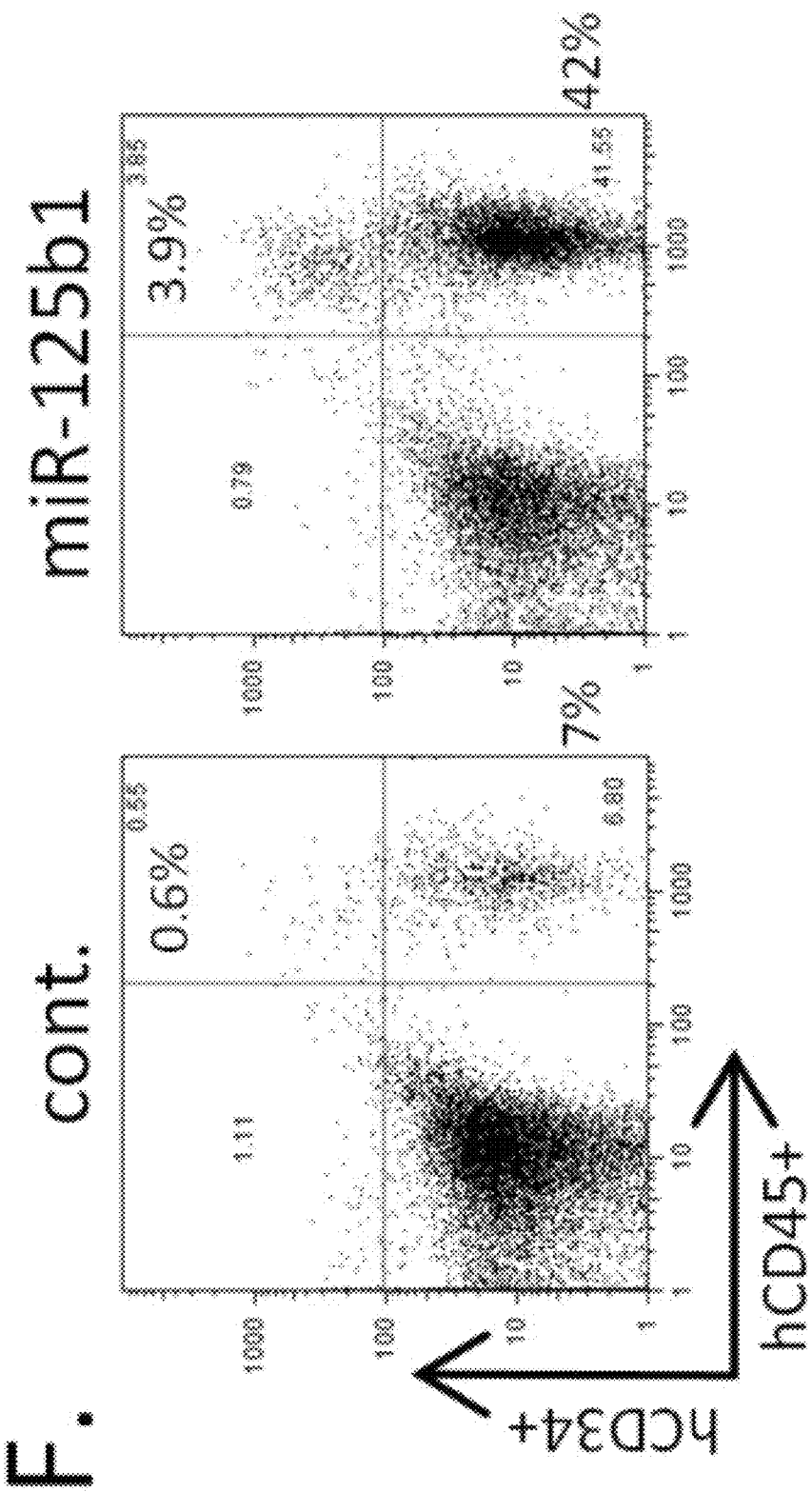
Figure 9:
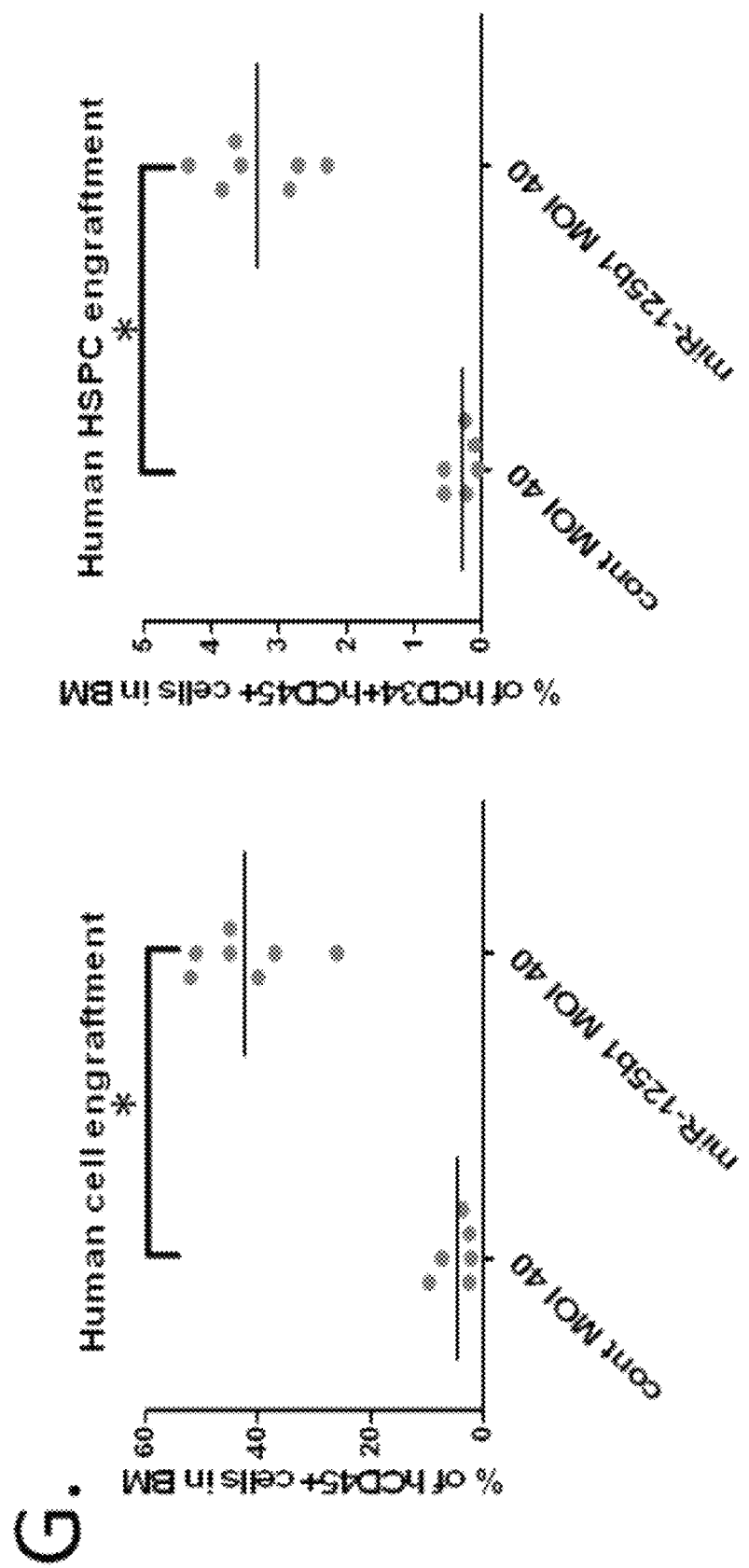

To determine whether miR-125b could also impact human hematopoietic engraftment, human CD34+ CB cells were transduced with control or a miR-125b1-expressing lentiviral vector at an MOI of about 4 or 40 (FIG. 9B) and subsequently injected intrahepatically into newborn Rag2−/−γc−/− mice on a BALB/c genetic background generating the human immune system (HIS) model previously described in Traggiai et al. Science (2004). miR-125b levels were assayed by qPCR. After 10 weeks, peripheral blood was collected and analyzed for the presence of human CD45+ WBCs by FACS, and a dose-dependent enhancement in multilineage engraftment was observed in miR-125b1-expressing vs. control HIS mice (FIG. 9C-E). At 12 week postreconstitution, the high-dose (multiplicity of infection [MOI 40]) groups were harvested and analyzed by FACS for the expression of different lineage markers including CD19 (B cells) and CD33 (myeloid). miR-125b-expressing HIS mice had significantly elevated levels of human (h)CD45+ cells and hCD34+ HSPCs in their bone marrow (FIGS. 9 F-G). These results show that miR-125b also promotes hematopoietic engraftment of human HSCs.

Example 5

Treatment of Myeloid Leukemia

This example illustrates the treatment of a patient suffering from or at risk of developing myeloid leukemia.

A patient suffering from or at risk of developing myeloid leukemia is identified and administered an effective amount of an antisense miR-125b oligonucleotide. The miR-125b oligonucleotide is administered to the patient by contacting HSCs of the patient with an expression construct containing a nucleic acid encoding the antisense miR-125 oligonucleotide. The expression construct express the antisense miR-125 oligonucleotide in the HSCs, thereby inhibiting proliferation of myeloid cells in the patient. The appropriate dosage (i.e., the expression level of the antisense miR-125 oligonucleotide from the expression construct) and treatment regimen can be readily determined by skilled artisans based on a number of factors including, but not limited to, the route of administration and the patient's disease state. The treatment efficacy is evaluated by observing delay or slowing of disease progression, amelioration or palliation of the disease state, and remission.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for increasing blood output in a mammal, comprising:
providing a mammal in need of increasing blood output; and
administering an oligonucleotide comprising a microRNA-125b (miR-125b) sequence to hematopoietic stem cells (HSCs) in the mammal, thereby increased blood output in the mammal, wherein the miR-125b sequence comprises a mature miR-125b1 sequence, a mature miR-125b2 sequence, a pre-miR-125b1 sequence, or a pre-miR-125b2 sequence.

2. The method of claim 1, wherein the oligonucleotide comprises a nucleic acid sequence encoding a miR-125b selected from the group consisting of SEQ ID NOs: 1-3 and 5-6.

3. The method of claim 1, wherein administering the oligonucleotide to the HSCs comprises contacting the HSCs with an expression construct comprising the oligonucleotide, thereby the miR-125b is expressed in the HSCs.

4. The method of claim 1, further comprising measuring production of blood cells in the mammal.

5. The method of claim 4, wherein the blood cells are selected from the group consisting of red blood cells, white blood cells, platelets, and any combination thereof.

6. The method of claim 4, wherein measuring production of blood cells comprises measuring the number of the peripheral blood cells in the mammal.

7. The method of claim 1, wherein the mammal suffers from low blood counts.

8. The method of claim 1, wherein the mammal suffers from a disease or disorder selected from the group consisting of myelosuppression, pancytopenia, anemia, thrombocytopenia, leucopenia, neutropenia, and granulocytopenia.

9. A method for promoting hematopoietic stem cell engraftment in a mammal in need thereof, comprising:
administering an oligonucleotide comprising a microRNA-125b (miR-125b) sequence to hematopoietic stem cells (HSCs) in the mammal, wherein the miR-125b sequence is a mature miR-125b1 sequence, a mature miR-125b2 sequence, a pre-miR-125b1 sequence, or a pre-miR-125b2 sequence; and
measuring proliferation of B cells, T cells, or myeloid cells in the mammal.

10. The method of claim 9, wherein the mammal suffers from low blood count, bone marrow failure disorders, or hematopoietic malignancies.

11. The method of claim 9, wherein the mammal suffers from aplastic anemia.

12. The method of claim 9, wherein administering the oligonucleotide to the HSCs comprises contacting the HSCs with an expression construct comprising oligonucleotide, thereby the miR-125b oligonucleotide is expressed in the HSCs.

13. The method of claim 9, wherein the oligonucleotide comprises a nucleic acid sequence encoding a miR-125b selected from the group consisting of SEQ ID NOs: 1-3 and 5-6.

* * * * *

UNITED STATES PATENT AND TRADEMARK OFFICE
CERTIFICATE OF CORRECTION

PATENT NO. : 9,006,195 B2  
APPLICATION NO. : 13/230673  
DATED : April 14, 2015  
INVENTOR(S) : David Baltimore and Ryan M. O'Connell Page 1 of 1

It is certified that error appears in the above-identified patent and that said Letters Patent is hereby corrected as shown below:

On the title page

In column 1 (page 1, item 56) at line 16, Under Other Publications, change "MicorRNAs." to --MicroRNAs.--.

In the specification

In column 1 at line 40, Change "mRNAs" to --miRNAs--.

In column 5 at line 56, Change ""mRNA-125b"" to --"miRNA-125b"--.

In column 10 at line 55, Change "thioridine," to --thiouridine,--.

In column 10 at lines 55-56, Change "5-carb 1 pseudouridine," to --5-carb-1-pseudouridine,--.

In column 10 at line 56, Change "galactosylqueosine," to --galactosylqueuosine,--.

In column 10 at lines 56-57, Change "2'-Omethylguanosine," to --2'-O-methylguanosine,--.

In column 10 at line 57, Change "isopente nyladenosine," to --isopentenyladenosine,--.

In column 10 at line 63, Change "mannosylqueosine," to --mannosylqueuosine,--.

In column 11 at line 2, Change "queosine," to --queuosine,--.

In column 14 at line 26, Change "p IND," to --pIND,--.

In column 14 at line 42, Change "phosphotranferase" to --phosphotransferase--.

In column 17 at lines 58-59, Change "down-regulated." to --downregulated.--.

In column 19 at line 33, Before "is" delete "miRNA".

In column 21 at line 25, Change "neage-negative" to --lineage-negative--.

In the claims

In column 52 at line 35 (approx.), In Claim 12, after "comprising" insert --the--.

Signed and Sealed this  
Fifteenth Day of December, 2015

Michelle K. Lee  
*Director of the United States Patent and Trademark Office*

SEQUENCE LISTING

```
<160> NUMBER OF SEQ ID NOS: 74

<210> SEQ ID NO 1
<211> LENGTH: 22
<212> TYPE: RNA
<213> ORGANISM: Homo sapiens

<400> SEQUENCE: 1
ucccugagac ccuaacuugu ga                                              22

<210> SEQ ID NO 2
<211> LENGTH: 88
<212> TYPE: RNA
<213> ORGANISM: Homo sapiens

<400> SEQUENCE: 2
ugcgcuccuc ucagucccug agacccuaac uugugauguu uaccguuuaa auccacgggu     60
uaggcucuug ggagcugcga gucgugcu                                        88

<210> SEQ ID NO 3
<211> LENGTH: 89
<212> TYPE: RNA
<213> ORGANISM: Homo sapiens

<400> SEQUENCE: 3
accagacuuu uccuaguccc ugagacccua acuugugagg uauuuuagua acaucacaag     60
ucaggcucuu gggaccuagg cggagggga                                       89

<210> SEQ ID NO 4
<211> LENGTH: 8
<212> TYPE: RNA
<213> ORGANISM: Homo sapiens

<400> SEQUENCE: 4 cccugaga                                                              8

<210> SEQ ID NO 5
<211> LENGTH: 22
<212> TYPE: RNA
<213> ORGANISM: Mus musculus
```

```
<400> SEQUENCE: 5
ucccugagac ccuaacuugu ga                                             22

<210> SEQ ID NO 6
<211> LENGTH: 77
<212> TYPE: RNA
<213> ORGANISM: Mus musculus

<400> SEQUENCE: 6 ugcgucccc ucaguccug agacccuaac uugugauguu uaccguuuaa auccacgggu      60
uaggcucuug ggagcug                                                   77

<210> SEQ ID NO 7
<211> LENGTH: 8
<212> TYPE: RNA
<213> ORGANISM: Mus musculus

<400> SEQUENCE: 7 cccugaga                                                             8

<210> SEQ ID NO 8
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 8
agggacucug ggauugaaca cu                                             22

<210> SEQ ID NO 9
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 9
agggacucug ggauugaaca cu                                             22

<210> SEQ ID NO 10
<211> LENGTH: 88
<212> TYPE: RNA
<213> ORGANISM: Artificial Sequence
<220> FEATURE:
<223> OTHER INFORMATION: Synthetic oligonucleotide

<400> SEQUENCE: 10
acgcgaggag agucagggac ucugggauug aacacuacaa auggcaaauu uaggugccca    60
auccgagaac ccucgacgcu cagcacga                                       88

<210> SEQ ID NO 11
<211> LENGTH: 89
<212> TYPE: RNA
<213> ORGANISM: Artificial Sequence
<220> FEATURE:
<223> OTHER INFORMATION: Synthetic oligonucleotide

<400> SEQUENCE: 11
uggucugaaa aggaucaggg acucugggau ugaacacucc auaaaaucau uguaguguuc    60
aguccgagaa cccuggaucc gccuccccu                                      89
```

```
<210> SEQ ID NO 12
<211> LENGTH: 77
<212> TYPE: RNA
<213> ORGANISM: Artificial Sequence
<220> FEATURE:
<223> OTHER INFORMATION: Synthetic oligonucleotide

<400> SEQUENCE: 12
acgcgagggg agucagggac ucugggauug aacacuacaa auggcaaauu uaggugccca    60
auccgagaac ccucgac                                                   77

<210> SEQ ID NO 13
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 13 gggacucu                                                              8

<210> SEQ ID NO 14
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 14 gggacucu                                                              8

<210> SEQ ID NO 15
<211> LENGTH: 22
<212> TYPE: RNA
<213> ORGANISM: Homo sapiens

<400> SEQUENCE: 15
ucguaccgug aguaauaaug cg                                              22

<210> SEQ ID NO 16
<211> LENGTH: 85
<212> TYPE: RNA
<213> ORGANISM: Homo sapiens

<400> SEQUENCE: 16
cgcuggcgac gggacauuau uacuuuuggu acgcgcugug acacuucaaa cucguaccgu    60
gaguaauaau gcgccgucca cggca                                          85

<210> SEQ ID NO 17
<211> LENGTH: 21
<212> TYPE: RNA
<213> ORGANISM: Homo sapiens

<400> SEQUENCE: 17
cauuauuacu uuugguacgc g                                              21

<210> SEQ ID NO 18
<211> LENGTH: 8
<212> TYPE: RNA
<213> ORGANISM: Homo sapiens

<400> SEQUENCE: 18 cguaccgu                                                              8
```

```
<210> SEQ ID NO 19
<211> LENGTH: 8
<212> TYPE: RNA
<213> ORGANISM: Homo sapiens

<400> SEQUENCE: 19 auuauuac                                                                  8

<210> SEQ ID NO 20
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 20
agcauggcac ucauuauuac gc                                                 22

<210> SEQ ID NO 21
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 21
guaauaauga aaccaugcg c                                                   21

<210> SEQ ID NO 22
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 22 gcauggca                                                                  8

<210> SEQ ID NO 23
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 23 uaauaaug                                                                  8

<210> SEQ ID NO 24
<211> LENGTH: 73
<212> TYPE: RNA
<213> ORGANISM: Mus musculus

<400> SEQUENCE: 24
ugacagcaca uuauuacuuu ugguacgcgc ugugacacuu caaacucgua ccgugaguaa         60
uaaugcgcgg uca                                                           73

<210> SEQ ID NO 25
<211> LENGTH: 21
<212> TYPE: RNA
<213> ORGANISM: Mus musculus

<400> SEQUENCE: 25
cauuauuacu uuugguacgc g                                                  21
```

```
<210> SEQ ID NO 26
<211> LENGTH: 8
<212> TYPE: RNA
<213> ORGANISM: Mus musculus

<400> SEQUENCE: 26 auuauuac                                                                8

<210> SEQ ID NO 27
<211> LENGTH: 22
<212> TYPE: RNA
<213> ORGANISM: Mus musculus

<400> SEQUENCE: 27
ucguaccgug aguaauaaug cg                                               22

<210> SEQ ID NO 28
<211> LENGTH: 8
<212> TYPE: RNA
<213> ORGANISM: Mus musculus

<400> SEQUENCE: 28 cguaccgu                                                                8

<210> SEQ ID NO 29
<211> LENGTH: 65
<212> TYPE: RNA
<213> ORGANISM: Homo sapiens

<400> SEQUENCE: 29 cguuaaugc uaaucgugau aggggutuuu gccuccaacu gacuccuaca uauuagcauu        60
aacag                                                                  65

<210> SEQ ID NO 30
<211> LENGTH: 23
<212> TYPE: RNA
<213> ORGANISM: Homo sapiens

<400> SEQUENCE: 30
uuaaugcuaa ucgugauagg ggu                                              23

<210> SEQ ID NO 31
<211> LENGTH: 8
<212> TYPE: RNA
<213> ORGANISM: Homo sapiens

<400> SEQUENCE: 31 uaaugcua                                                                8

<210> SEQ ID NO 32
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 32
aauuacgauu agcacuaucc cca                                              23

<210> SEQ ID NO 33
<211> LENGTH: 65
<212> TYPE: RNA
```

<213> ORGANISM: Mus musculus

<400> SEQUENCE: 33
cuguuaaugc uaauugugau aggggguuuug gccucugacu gacuccuacc uguuagcauu    60
aacag                                                                 65

<210> SEQ ID NO 34
<211> LENGTH: 23
<212> TYPE: RNA
<213> ORGANISM: Mus musculus

<400> SEQUENCE: 34
uuaaugcuaa uugugauagg ggu                                             23

<210> SEQ ID NO 35
<211> LENGTH: 8
<212> TYPE: RNA
<213> ORGANISM: Mus musculus

<400> SEQUENCE: 35 uaaugcua                                                              8

<210> SEQ ID NO 36
<211> LENGTH: 84
<212> TYPE: RNA
<213> ORGANISM: Homo sapiens

<400> SEQUENCE: 36
acuggucggu gauuuaggua guuuccuguu guugggaucc accuuucucu cgacagcacg    60
acacugccuu cauuacuuca guug                                            84

<210> SEQ ID NO 37
<211> LENGTH: 22
<212> TYPE: RNA
<213> ORGANISM: Homo sapiens

<400> SEQUENCE: 37
uagguaguuu ccuguuguug gg                                              22

<210> SEQ ID NO 38
<211> LENGTH: 22
<212> TYPE: RNA
<213> ORGANISM: Homo sapiens

<400> SEQUENCE: 38
ucgacagcac gacacugccu uc                                              22

<210> SEQ ID NO 39
<211> LENGTH: 85
<212> TYPE: RNA
<213> ORGANISM: Mus musculus

<400> SEQUENCE: 39
aacuggucgg ugauuuaggu aguuuccugu uguugggauc caccuuucuc ucgacagcac    60
gacacugccu ucauuacuuc aguug                                           85

<210> SEQ ID NO 40
<211> LENGTH: 22
<212> TYPE: RNA
<213> ORGANISM: Mus musculus

<400> SEQUENCE: 40

```
uagguaguuu ccuguuguug gg                                              22
```

<210> SEQ ID NO 41
<211> LENGTH: 22
<212> TYPE: RNA
<213> ORGANISM: Mus musculus

<400> SEQUENCE: 41

```
ucgacagcac gacacugccu uc                                              22
```

<210> SEQ ID NO 42
<211> LENGTH: 110
<212> TYPE: RNA
<213> ORGANISM: Homo sapiens

<400> SEQUENCE: 42

```
cggaaaauuu gccaaggguu uggggaaca uucaaccugu cggugaguuu gggcagcuca      60
ggcaaaccau cgaccguuga guggacccug aggccuggaa uugccauccu                110
```

<210> SEQ ID NO 43
<211> LENGTH: 22
<212> TYPE: RNA
<213> ORGANISM: Homo sapiens

<400> SEQUENCE: 43

```
aacauucaac cugucggcuga gu                                             22
```

<210> SEQ ID NO 44
<211> LENGTH: 22
<212> TYPE: RNA
<213> ORGANISM: Homo sapiens

<400> SEQUENCE: 44

```
aaccaucgac cguugagugg ac                                              22
```

<210> SEQ ID NO 45
<211> LENGTH: 89
<212> TYPE: RNA
<213> ORGANISM: Mus musculus

<400> SEQUENCE: 45

```
gccaaggguu uggggaaca uucaaccugu cggugaguuu gggcagcuca gacaaaccau      60
cgaccguuga guggaccccg aggccugga                                       89
```

<210> SEQ ID NO 46
<211> LENGTH: 22
<212> TYPE: RNA
<213> ORGANISM: Mus musculus

<400> SEQUENCE: 46

```
aacauucaac cugucggcuga gu                                             22
```

<210> SEQ ID NO 47
<211> LENGTH: 22
<212> TYPE: RNA
<213> ORGANISM: Mus musculus

<400> SEQUENCE: 47

```
accaucgacc guugagugga cc                                              22
```

<210> SEQ ID NO 48

```
<211> LENGTH: 79
<212> TYPE: RNA
<213> ORGANISM: Homo sapiens

<400> SEQUENCE: 48
cccgggcuga gguaggaggu uguauaguug aggaggacac ccaaggagau cacuauacgg      60
ccuccuagcu uucccccagg                                                 79

<210> SEQ ID NO 49
<211> LENGTH: 22
<212> TYPE: RNA
<213> ORGANISM: Homo sapiens

<400> SEQUENCE: 49
ugagguagga gguuguauag uu                                              22

<210> SEQ ID NO 50
<211> LENGTH: 22
<212> TYPE: RNA
<213> ORGANISM: Homo sapiens

<400> SEQUENCE: 50
cuauacggcc uccuagcuuu cc                                              22

<210> SEQ ID NO 51
<211> LENGTH: 93
<212> TYPE: RNA
<213> ORGANISM: Mus musculus

<400> SEQUENCE: 51 cgcgccccccc gggcugaggu aggagguugu auaguugagg aagacacccg aggagaucac    60
uauacggccu ccuagcuuuc cccaggcugc gcc                                  93

<210> SEQ ID NO 52
<211> LENGTH: 22
<212> TYPE: RNA
<213> ORGANISM: Mus musculus

<400> SEQUENCE: 52
ugagguagga gguuguauag uu                                              22

<210> SEQ ID NO 53
<211> LENGTH: 22
<212> TYPE: RNA
<213> ORGANISM: Mus musculus

<400> SEQUENCE: 53
cuauacggcc uccuagcuuu cc                                              22

<210> SEQ ID NO 54
<211> LENGTH: 97
<212> TYPE: RNA
<213> ORGANISM: Homo sapiens

<400> SEQUENCE: 54
cagaucucag acaucucggg gaucaucaug ucacgagaua ccagugugca cuugugacag     60
auugauaacu gaaaggucug ggagccacuc aucuuca                              97

<210> SEQ ID NO 55
<211> LENGTH: 23
<212> TYPE: RNA
<213> ORGANISM: Homo sapiens
```

```
<400> SEQUENCE: 55
ucggggauca ucaugucacg aga                                           23

<210> SEQ ID NO 56
<211> LENGTH: 22
<212> TYPE: RNA
<213> ORGANISM: Homo sapiens

<400> SEQUENCE: 56
ugugacagau ugauaacuga aa                                            22

<210> SEQ ID NO 57
<211> LENGTH: 73
<212> TYPE: RNA
<213> ORGANISM: Mus musculus

<400> SEQUENCE: 57
ccgggccuag guucugugau acacuccgac ucgggcucug gagcagucag ugcaugacag   60
aacuugggcc cgg                                                      73

<210> SEQ ID NO 58
<211> LENGTH: 21
<212> TYPE: RNA
<213> ORGANISM: Mus musculus

<400> SEQUENCE: 58
ucagugcaug acagaacuug g                                             21

<210> SEQ ID NO 59
<211> LENGTH: 24
<212> TYPE: RNA
<213> ORGANISM: Mus musculus

<400> SEQUENCE: 59
uagguucugu gauacacucc gacu                                          24

<210> SEQ ID NO 60
<211> LENGTH: 96
<212> TYPE: DNA
<213> ORGANISM: Artificial Sequence
<220> FEATURE:
<223> OTHER INFORMATION: miR-125a 155-formatted template

<400> SEQUENCE: 60
gaaggctgta tgctgtccct gagacccttt aacctgtgag ttttggccac tgactgactc   60
acaggtaagg gtctcaggga caggacacaa ggcctg                             96

<210> SEQ ID NO 61
<211> LENGTH: 92
<212> TYPE: DNA
<213> ORGANISM: Artificial Sequence
<220> FEATURE:
<223> OTHER INFORMATION: miR-125b 155-formatted template

<400> SEQUENCE: 61
gaaggctgta tgctgtccct gagaccctaa cttgtgagtt ttggccactg actgactcac   60
aagtgggtct caggacagg acacaaggcc tg                                  92

<210> SEQ ID NO 62
<211> LENGTH: 90
<212> TYPE: DNA
```

<213> ORGANISM: Artificial Sequence
<220> FEATURE:
<223> OTHER INFORMATION: miR-155 155-formatted template

<400> SEQUENCE: 62

```
gaaggctgta tgctgttaat gctaattgtg atagggcttt tggccactga ctgacccta      60 tcaattagca ttaacaggac acaaggcctg                                       90
```

<210> SEQ ID NO 63
<211> LENGTH: 92
<212> TYPE: DNA
<213> ORGANISM: Artificial Sequence
<220> FEATURE:
<223> OTHER INFORMATION: miR-99a 155-formatted template

<400> SEQUENCE: 63

```
gaaggctgta tgctgaaccc gtagatccga tcttgtggtt ttggccactg actgaccaca      60
agatgatcta cgggttcagg acacaaggcc tg                                    92
```

<210> SEQ ID NO 64
<211> LENGTH: 90
<212> TYPE: DNA
<213> ORGANISM: Artificial Sequence
<220> FEATURE:
<223> OTHER INFORMATION: miR-126 155-formatted template

<400> SEQUENCE: 64

```
gaaggctgta tgctgcatta ttacttttgg tacgcggttt tggccactga ctgaccgcgt      60
accaagtaat aatgcaggac acaaggcctg                                       90
```

<210> SEQ ID NO 65
<211> LENGTH: 92
<212> TYPE: DNA
<213> ORGANISM: Artificial Sequence
<220> FEATURE:
<223> OTHER INFORMATION: miR-196b 155-formatted template

<400> SEQUENCE: 65

```
gaaggctgta tgctgtaggt agtttcctgt tgttggggtt ttggccactg actgacccca      60
acaaggaaac tacctacagg acacaaggcc tg                                    92
```

<210> SEQ ID NO 66
<211> LENGTH: 92
<212> TYPE: DNA
<213> ORGANISM: Artificial Sequence
<220> FEATURE:
<223> OTHER INFORMATION: miR-130a 155-formatted template

<400> SEQUENCE: 66

```
gaaggctgta tgctgcagtg caatgttaaa agggcatgtt ttggccactg actgacatgc      60
ccttaacatt gcactgcagg acacaaggcc tg                                    92
```

<210> SEQ ID NO 67
<211> LENGTH: 92
<212> TYPE: DNA
<213> ORGANISM: Artificial Sequence
<220> FEATURE:
<223> OTHER INFORMATION: miR-542-5p 155-formatted template

<400> SEQUENCE: 67

```
gaaggctgta tgctgctcgg ggatcatcat gtcacgagtt ttggccactg actgactcgt      60
gacaatgatc cccgagcagg acacaaggcc tg                                    92
```

```
<210> SEQ ID NO 68
<211> LENGTH: 92
<212> TYPE: DNA
<213> ORGANISM: Artificial Sequence
<220> FEATURE:
<223> OTHER INFORMATION: miR-181c 155-formatted template

<400> SEQUENCE: 68
gaaggctgta tgctgaacat tcaacctgtc ggtgagtgtt ttggccactg actgacactc      60
accgaggttg aatgttcagg acacaaggcc tg                                    92

<210> SEQ ID NO 69
<211> LENGTH: 92
<212> TYPE: DNA
<213> ORGANISM: Artificial Sequence
<220> FEATURE:
<223> OTHER INFORMATION: miR-193b 155-formatted template

<400> SEQUENCE: 69
gaaggctgta tgctgaactg gcccacaaag tcccgctgtt ttggccactg actgacagcg      60
ggactgtggg ccagttcagg acacaaggcc tg                                    92

<210> SEQ ID NO 70
<211> LENGTH: 92
<212> TYPE: DNA
<213> ORGANISM: Artificial Sequence
<220> FEATURE:
<223> OTHER INFORMATION: let7e 155-formatted template

<400> SEQUENCE: 70
gaaggctgta tgctgtgagg taggaggttg tatagttgtt ttggccactg actgacaact      60 atccctcct acctcacagg acacaaggcc tg                                     92

<210> SEQ ID NO 71
<211> LENGTH: 43
<212> TYPE: DNA
<213> ORGANISM: Artificial Sequence
<220> FEATURE:
<223> OTHER INFORMATION: miR-125b-1 NotI Fw

<400> SEQUENCE: 71
ttcgcggccg cgagttttct ctgatgtact cgtgatcgta tgt                        43

<210> SEQ ID NO 72
<211> LENGTH: 34
<212> TYPE: DNA
<213> ORGANISM: Artificial Sequence
<220> FEATURE:
<223> OTHER INFORMATION: miR-125b-1 XhoI Rev

<400> SEQUENCE: 72
ttcctcgaga acagaaatcc aggagctgcc actc                                  34

<210> SEQ ID NO 73
<211> LENGTH: 35
<212> TYPE: DNA
<213> ORGANISM: Artificial Sequence
<220> FEATURE:
<223> OTHER INFORMATION: miR-125b-2 NotI Fw

<400> SEQUENCE: 73
ttcgcggccg cgcccttgct agcgaagcag atttt                                 35
```

```
<210> SEQ ID NO 74
<211> LENGTH: 35
<212> TYPE: DNA
<213> ORGANISM: Artificial Sequence
<220> FEATURE:
<223> OTHER INFORMATION: miR125b-2 XhoI Rev

<400> SEQUENCE: 74
ttcctcgaga gtatttttgg ggatgggtca tggtg                              35
```